United States Patent [19]

Godfrey, Jr. et al.

[11] Patent Number: 4,604,402

[45] Date of Patent: Aug. 5, 1986

[54] HYDROXY SUBSTITUTED UREIDO AMINO AND IMINO ACIDS

[75] Inventors: Jollie D. Godfrey, Jr., Lawrenceville; Eric M. Gordon, Pennington; Sesha I. Natarajan, Neshanic Station, all of N.J.

[73] Assignee: E. R. Squibb & Sons, Inc., Princeton, N.J.

[21] Appl. No.: 595,218

[22] Filed: Mar. 30, 1984

[51] Int. Cl.$^4$ .................. C07D 207/04; C07D 207/20; A61K 31/40; A61K 31/44

[52] U.S. Cl. ..................................... 514/333; 514/339; 514/341; 514/343; 514/397; 514/414; 514/423; 546/147; 546/256; 546/268; 546/273; 546/276; 546/281; 548/188; 548/336; 548/356; 548/454; 548/455; 548/456; 548/463; 548/467; 548/468; 548/517; 548/525; 548/527; 548/533; 548/534; 548/409; 548/953; 560/34; 560/16; 562/439; 562/426

[58] Field of Search ................ 424/274; 548/533, 534, 548/336, 356, 454, 455, 456, 467, 468, 517, 527; 514/423, 339, 341, 343, 397, 414

[56] References Cited

U.S. PATENT DOCUMENTS 4,402,969  9/1983  Greenlee et al. ............... 548/533 X
4,470,973  9/1984  Natarajan et al. .............. 546/245 X
4,474,778  10/1984 Gordon et al. ................... 424/244
4,500,518  2/1985  Gordon et al. ................... 514/2
4,514,391  4/1985  Gordon et al. ................... 514/2

OTHER PUBLICATIONS

Meyer et al., "Angiotensin Converting Enzyme Inhibitors . . . " J. Med. Chem., vol. 25, pp. 996-999 (1982).

Primary Examiner—Joseph Paul Brust
Attorney, Agent, or Firm—Lawrence S. Levinson; Stephen B. Davis

[57] ABSTRACT

Compounds of the formula

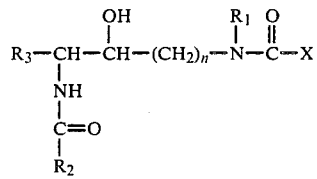

are disclosed. These compounds are useful as hypotensive agents due to their angiotensin converting enzyme inhibition activity and depending upon the definition of X may also be useful as analgesics due to their enkephalinase inhibition activity.

13 Claims, No Drawings

HYDROXY SUBSTITUTED UREIDO AMINO AND IMINO ACIDS

BACKGROUND OF THE INVENTION

Natarajan et al. in U.S. patent applications Ser. No. 400,798 filed July 22, 1982 and Ser. No. 513,931 filed July 14, 1983 discloses acylalkylaminocarbonyl substituted amino and imino acid compounds of the formula

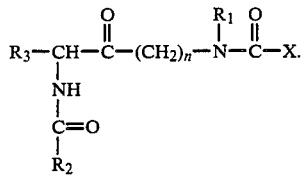

These compounds are disclosed as possessing angiotensin converting enzyme inhibition activity and in some cases, depending upon the definition of X, also possessing enkephalinase inhibition activity.

SUMMARY OF THE INVENTION

The novel hydroxy substituted ureido amino and imino acids, esters and salts of this invention are of the formula

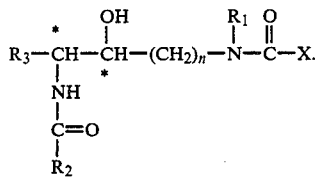

X is an amino or imino acid or ester of the formula

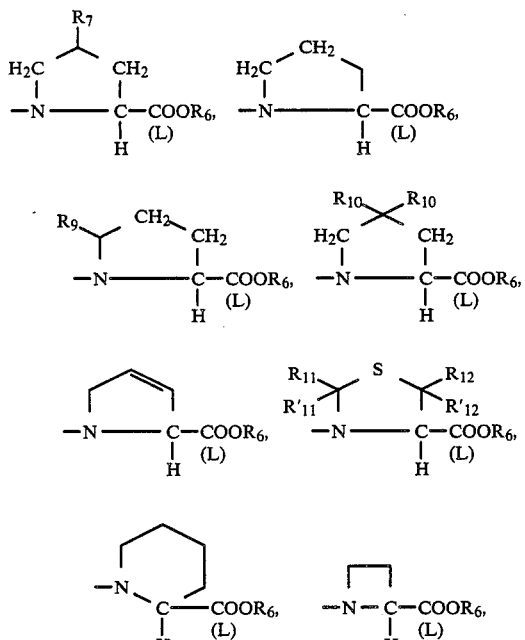

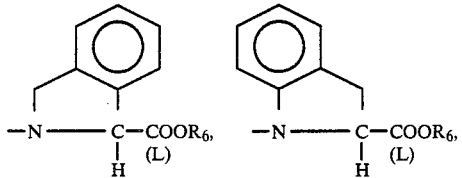

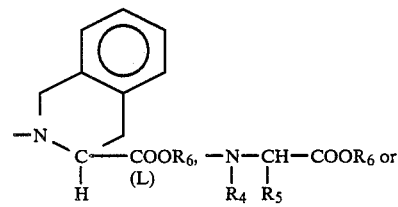

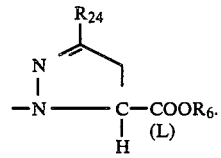

$R_7$ is hydrogen, lower alkyl, halogen, keto, hydroxy,

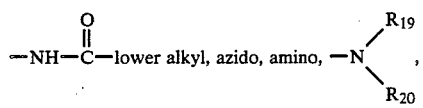

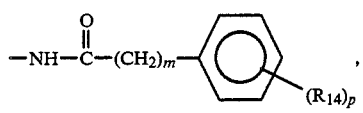

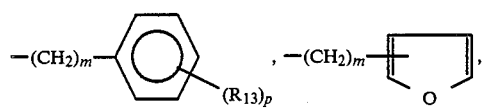

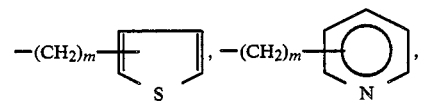

a 1- or 2-naphthyl of the formula

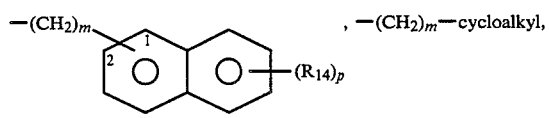

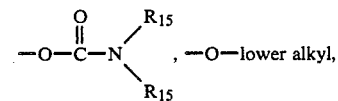

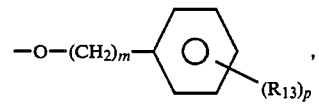

a 1- or 2-naphthyloxy of the formula

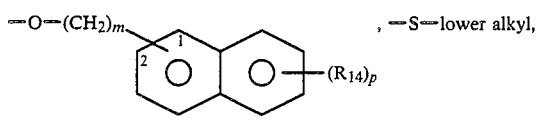 , —S—lower alkyl,

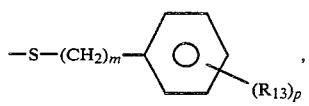

or a 1- or 2-naphthylthio of the formula

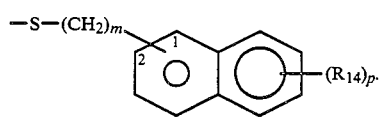

$R_8$ is keto, halogen, 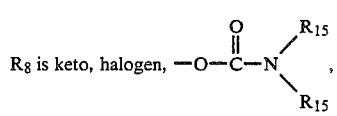

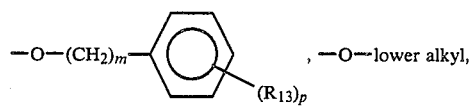 , —O—lower alkyl, a 1- or 2-naphthyloxy of the formula

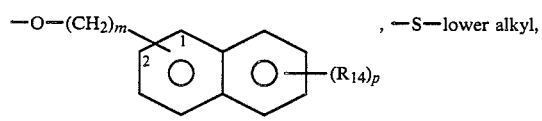 , —S—lower alkyl,

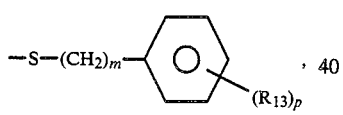

or a 1- or 2-naphthylthio of the formula

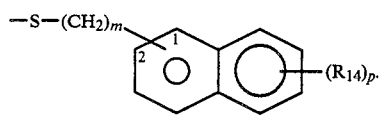

$R_9$ is keto or 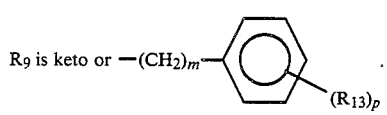

$R_{10}$ is halogen or -Y-$R_{16}$.

$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

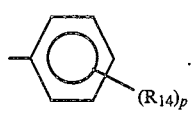

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two, three, or four.

p is one, two or three provided that p is more than one only if $R_{13}$ or $R_{14}$ is hydrogen, methyl, methoxy, chloro, or fluoro.

$R_{15}$ is hydrogen or lower alkyl of 1 to 4 carbons.

Y is oxygen or sulfur.

$R_{16}$ is lower alkyl of 1 to 4 carbons,

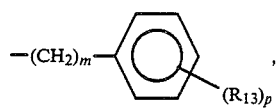

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_{19}$ is lower alkyl, benzyl, or phenethyl.

$R_{20}$ is hydrogen, lower alkyl, benzyl or phenethyl.

$R_5$ is hydrogen, lower alkyl,

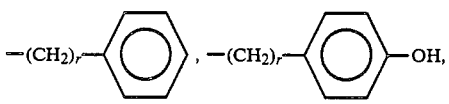

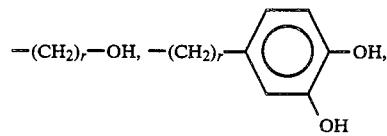

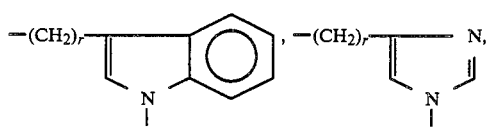

—$(CH_2)_r$—$NH_2$, —$(CH_2)_r$—SH, —$(CH_2)_r$—S—lower alkyl,

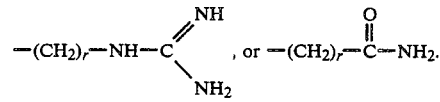

r is an integer from 1 to 4.

$R_4$ is hydrogen, lower alkyl,

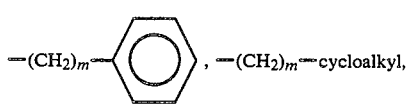

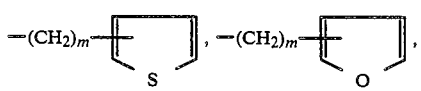

-continued

—(CH$_2$)$_{\overline{m}}$-pyridyl, -bicyclohexyl- or indanyl.

n is one or two.

R$_1$ is hydrogen, lower alkyl, halo substituted lower alkyl,

—(CH$_2$)$_{\overline{m}}$-phenyl(R$_{14}$)$_p$, —(CH$_2$)$_{\overline{m}}$-thienyl, —(CH$_2$)$_{\overline{m}}$-furyl, —(CH$_2$)$_{\overline{m}}$-pyridyl, —(CH$_2$)$_{\overline{m}}$-cycloalkyl, —(CH$_2$)$_{\overline{2}}$-NH$_2$,
—(CH$_2$)$_{\overline{3}}$-NH$_2$, —(CH$_2$)$_{\overline{4}}$-NH$_2$, —(CH$_2$)$_{\overline{r}}$-phenyl-OH with OH, —(CH$_2$)$_{\overline{r}}$-indolyl, —(CH$_2$)$_{\overline{r}}$-imidazolyl, —(CH$_2$)$_{\overline{r}}$-SH, —(CH$_2$)$_{\overline{r}}$-OH, —(CH$_2$)$_{\overline{r}}$-S-lower alkyl, —(CH$_2$)$_{\overline{r}}$-NH-C(=NH)NH$_2$, or —(CH$_2$)$_{\overline{r}}$-C(=O)-NH$_2$.

R$_2$ is —(CH$_2$)$_{\overline{m}}$-phenyl(R$_{14}$)$_p$, —(CH$_2$)$_{\overline{m}}$-thienyl, —(CH$_2$)$_{\overline{m}}$-furyl, or —(CH$_2$)$_{\overline{m}}$-pyridyl.

R$_3$ is hydrogen, lower alkyl,

—(CH$_2$)$_{\overline{m}}$-phenyl(R$_{14}$)$_p$, —(CH$_2$)$_{\overline{m}}$-thienyl, —(CH$_2$)$_{\overline{m}}$-furyl, —(CH$_2$)$_{\overline{m}}$-pyridyl, halo substituted lower alkyl, —(CH$_2$)$_{\overline{m}}$-cycloalkyl, —(CH$_2$)$_{\overline{r}}$-phenyl-OH with OH, —(CH$_2$)$_{\overline{r}}$-indolyl, —(CH$_2$)$_{\overline{r}}$-imidazolyl, —(CH$_2$)$_{\overline{r}}$-NH$_2$, —(CH$_2$)$_{\overline{r}}$-SH, —(CH$_2$)$_{\overline{r}}$-S-lower alkyl, —(CH$_2$)$_{\overline{r}}$-NH-C(=NH)NH$_2$, —(CH$_2$)$_{\overline{r}}$-C(=O)-NH$_2$ or —(CH$_2$)$_{\overline{r}}$-OH.

R$_6$ is hydrogen, lower alkyl, benzyl, benzhydryl,

—CH(R$_{17}$)-O-C(=O)-R$_{18}$, —C(R$_{21}$)(R$_{22}$)-C(=O)-O-R$_{23}$, —CH-(CH$_2$-OH)$_2$,

—CH$_2$-CH(OH)-CH$_2$-OH, —(CH$_2$)$_2$-N(CH$_3$)$_2$,

—CH$_2$-pyridyl, or a salt forming ion.

R$_{17}$ is hydrogen, lower alkyl, cycloalkyl, or phenyl.
R$_{18}$ is hydrogen, lower alkyl, lower alkoxy, or phenyl or R$_{17}$ and R$_{18}$ taken together are —(CH$_2$)$_2$—, —(CH$_2$)$_3$—, —CH=CH—, or o-xylyl.

R$_{21}$ and R$_{22}$ are independently selected from hydrogen and lower alkyl.
R$_{23}$ is lower alkyl.
R$_{24}$ is hydrogen, lower alkyl, —phenyl(R$_{14}$)$_p$, —thienyl, —furyl, or —pyridyl.

DETAILED DESCRIPTION OF THE INVENTION

This invention is directed to the various novel hydroxy substituted ureido amino and imino acid compounds of formula I above, and compositions and methods of using compositions containing these novel compounds.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

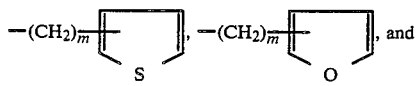, and

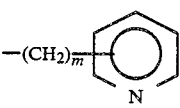

represent that the alkylene bridge is attached to an available carbon atom.

The compounds of formula I are obtained by treating a compound of the formula

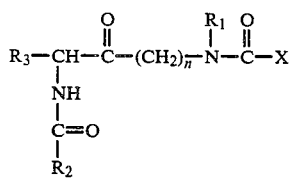 (II)

with a conventional reducing agent such as sodium borohydride, sodium cyanoborohydride, diisobutyl aluminum hydride, lithium tri t-butoxy aluminum hydride, etc.

The compounds of formula II can be prepared by various methods. For example, as taught by Natarajan et al. in the applications noted above, an acylated alkylamine of the formula

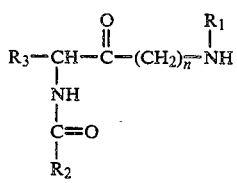 (III)

particularly the hydrochloride salt thereof can be coupled with the acid chloride of the formula

 (IV)

in the presence of N-methyl morpholine wherein $R_6$ in the definition of X is an easily removable ester protecting group such as benzyl or t-butyl. Removal of the $R_6$ protecting group such as by hydrogenation when $R_6$ is benzyl or treatment with trifluoroacetic acid when $R_6$ is t-butyl yields the products of formula I wherein $R_6$ is hydrogen.

The reactant of formula III can be prepared by reacting a keto compound of the formula

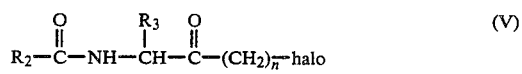 (V)

wherein halo is Cl or Br with an amine of the formula

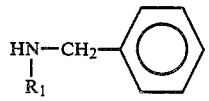

followed by hydrogenation to remove the benzyl protecting group.

The reactant of formula III can also be prepared by converting the carboxyalkylamine of the formula

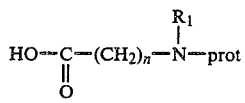

wherein prot is a protecting group such as benzyloxycarbonyl, to its acid chloride and then reacting with an oxazolone of the formula

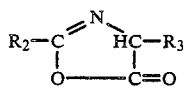

to yield

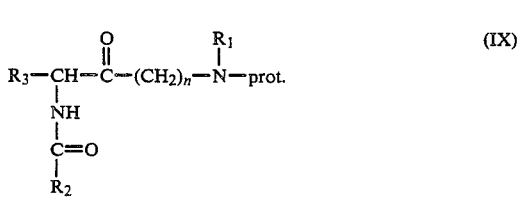 (IX)

Removal of the protecting group such as by hydrogenation yields the reactant of formula III.

The ketone intermediate of formula V can be prepared by treating a ketone of the formula

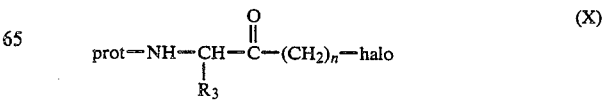 (X)

wherein prot is a protecting group such as benzyloxycarbonyl with hydrogen bromide and acetic acid followed by reaction with the acid halide of the formula

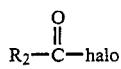 (XI)

in the presence of base such as sodium bicarbonate.

The compounds of formula II can also be obtained by reacting a carboxyalkylaminocarbonyl substituted amino or imino acid chloride of the formula

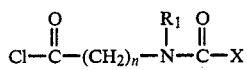 (XII)

wherein $R_6$ in the definition of X is an easily removable ester protecting group such as benzyl or t-butyl with the oxazolone of formula VIII. Removal of the $R_6$ ester group yields the compounds of formula I wherein $R_6$ is hydrogen.

The reactants of formula XII can be obtained by treating a substituted amine of the formula

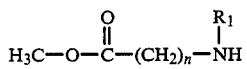 (XIII)

with the acid chloride of formula IV to yield

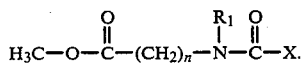

Treatment with methanol and sodium hydroxide, followed by oxalyl chloride yields the reactant of formula XII.

The acid chloride amino or imino acid ester of formula IV is prepared by treating the corresponding amino or imino acid ester hydrochloride with phosgene in the presence of N-methyl morpholine.

In the above reactions if any or all of $R_1$, $R_3$ and $R_5$ are

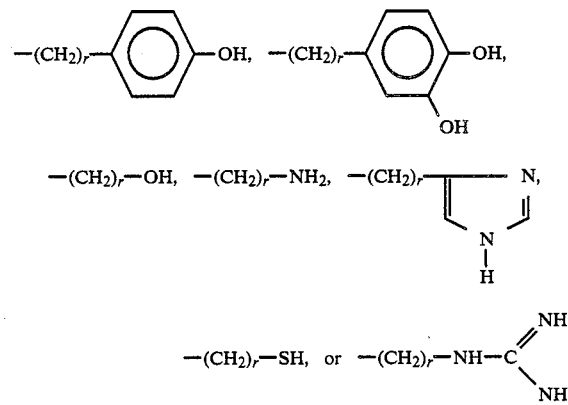

then the hydroxyl, amino, imidazolyl, mercaptan or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction sequence.

The ester products of formula I wherein $R_6$ is lower alkyl, benzyl or benzhydryl can be chemically treated such as with sodium hydroxide in aqueous dioxane or with trimethylsilylbromide to yield the products of formula I wherein $R_6$ is hydrogen. The benzyl and benzhydryl esters can also be hydrogenated, for example by treating with hydrogen in the presence of a palladium on carbon catalyst.

The ester products of formula I wherein $R_6$ is

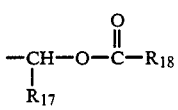

may be obtained by employing the acid chloride of formula IV in the above reactions with such ester group already in place. Such ester reactants can be prepared by treating the corresponding amino or imino acid of the formula

HX (XV)

wherein $R_6$ is hydrogen with an acid chloride such as

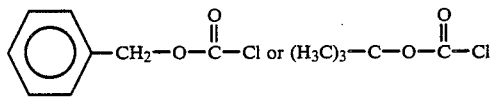

so as to protect the N-atom. The protected amino or imino acid is then reacted in the presence of a base with a compound of the formula

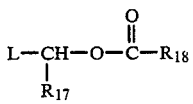 (XVI)

wherein L is a leaving group such as chlorine, bromine, tolylsulfonyl, etc., followed by removal of the N-protecting group such as by treatment with acid or hydrogenation.

The ester products of formula I wherein $R_6$ is

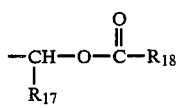

can also be obtained by treating the product of formula I wherein $R_6$ is hydrogen with a molar excess of the compound of formula XVI.

The ester products of formula I wherein $R_6$ is

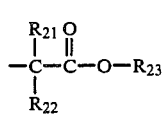

can be prepared by treating the product of formula I wherein $R_6$ is hydrogen with a molar excess of the compound of the formula

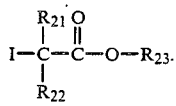 (XVII)

The ester products of formula I wherein $R_6$ is $-CH-(CH_2-OH)_2$ or

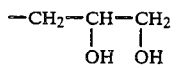

can be prepared by coupling the product of formula I wherein $R_6$ is hydrogen with a molar excess of the compound of the formula

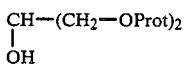 (XVIII)

or the formula

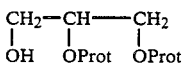

in the presence of a coupling agent such as dicyclohexylcarbodiimide followed by removal of the hydroxyl protecting groups.

Similarly, the ester products of formula I wherein $R_6$ is $-(CH_2)_2-N(CH_3)_2$ or

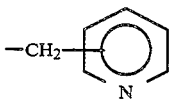

can be prepared by coupling the product of formula I wherein $R_6$ is hydrogen with a molar excess of the compound of the formula $$HO-CH_2-CH_2-N-(CH_3)_2 \quad (XX)$$

or the formula

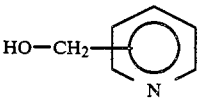 (XXI)

in the presence of a coupling agent such as dicyclohexylcarbodiimide.

The esters of formula I wherein $R_6$ is lower alkyl can be obtained from the carboxylic acid compounds, i.e., wherein $R_6$ is hydrogen, by conventional esterification procedures, e.g., treatment with an alkyl halide of the formula $R_6$—halo or an alcohol of the formula $R_6$—OH.

The products of formula I wherein $R_7$ is amino may be obtained by reducing the corresponding products of formula I wherein $R_7$ is azido.

Preferred compounds of this invention with respect to the amino or imino acid or ester part of the structure of formula I are those wherein:

$R_4$ is hydrogen, cyclohexyl, or phenyl.

$R_5$ is hydrogen, straight or branched chain lower alkyl or 1 to 4 carbons,

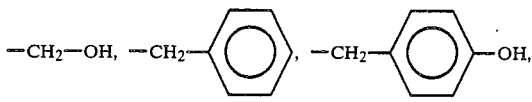

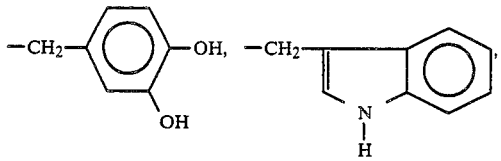

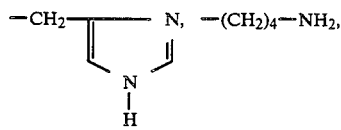

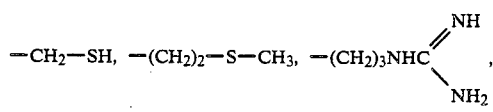

$R_6$ is hydrogen, straight or branched chain lower alkyl of 1 to 4 carbons, alkali metal salt,

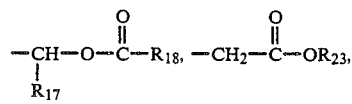

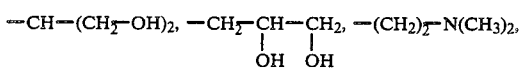

$R_{23}$ is straight or branched chain lower alkyl of 1 to 4 carbons, especially $-C(CH_3)_3$.

$R_{17}$ is hydrogen, straight or branched chain lower alkyl of 1 to 4 carbons, or cyclohexyl.

$R_{18}$ is straight or branched chain lower alkyl of 1 to 4 carbons or phenyl.

$R_7$ is hydrogen.

$R_7$ is hydroxy.

$R_7$ is straight or branched chain lower alkyl of 1 to 4 carbons or cyclohexyl.

$R_7$ is amino.

$R_7$ is —O—lower alkyl wherein lower alkyl is straight or branched chain of 1 to 4 carbons.

$R_7$ is

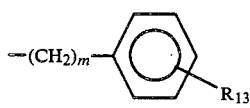

wherein m is zero, one or two and $R_{13}$ is hydrogen, methyl, methoxy, methylthio, chloro, bromo, fluoro, or hydroxy.

$R_7$ is

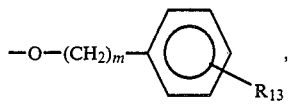

1-naphthyloxy or 2-naphthyloxy wherein m is zero, one, or two and $R_{13}$ is hydrogen, methyl, methoxy, methylthio, chloro, bromo, fluoro, or hydroxy.

$R_7$ is —S—lower alkyl wherein lower alkyl is straight or branched chain of 1 to 4 carbons.

$R_7$ is

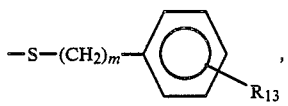

1-naphthylthio, or 2-naphthylthio wherein m is zero, one, or two and $R_{13}$ is hydrogen, methyl, methoxy, methylthio, chloro, bromo, fluoro, or hydroxy.

$R_8$ is —O—lower alkyl wherein lower alkyl is straight or branched chain of 1 to 4 carbons.

$R_8$ is

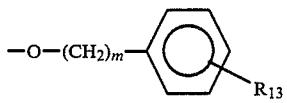

wherein m is zero, one, or two and $R_{13}$ is hydrogen, methyl, methoxy, methylthio, chloro, bromo, fluoro, or hydroxy.

$R_8$ is —S—lower alkyl wherein lower alkyl is straight or branched chain of 1 to 4 carbons.

$R_8$ is

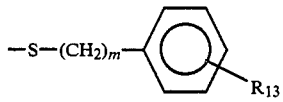

wherein m is zero, one or two and $R_{13}$ is hydrogen, methyl, methoxy, methylthio, chloro, bromo, fluoro or hydroxy.

$R_9$ is phenyl, 2-hydroxyphenyl, or 4-hydroxyphenyl.

$R_{10}$ are both fluoro or chloro.

$R_{10}$ are both —Y—$R_{16}$ wherein Y is O or S, $R_{16}$ is straight or branched chain lower alkyl of 1 to 4 carbons or the $R_{16}$ groups join to complete an unsubstituted 5- or 6-membered ring or said ring in which one or more of the available carbons has a methyl or dimethyl substituent.

$R_{11}$, $R'_{11}$, $R_{12}$ and $R'_{12}$ are all hydrogen, or $R_{11}$ is phenyl, 2-hydroxyphenyl, or 4-hydroxyphenyl and $R'_{11}$, $R_{12}$ and $R'_{12}$ are hydrogen.

$R_{24}$ is phenyl.

Most preferred compounds of this invention with respect to the amino or imino acid or ester part of the structure of formula I are those wherein:

X is

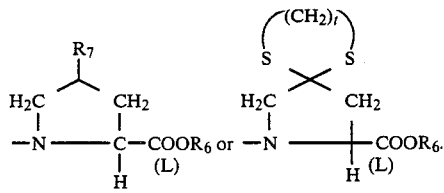

$R_6$ is hydrogen,

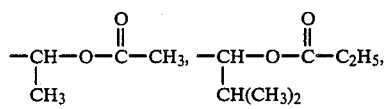

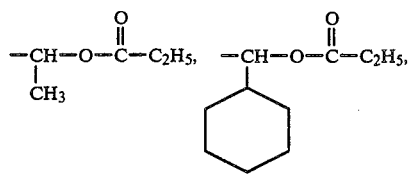

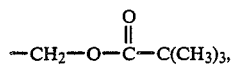

an alkali metal salt, straight or branched chain lower alkyl of 1 to 4 carbons, —(CH$_2$)$_2$N(CH$_3$)$_2$ or

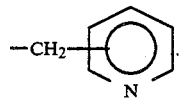

$R_7$ is hydrogen, cyclohexyl, lower alkoxy of 1 to 4 carbons,

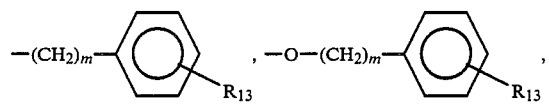

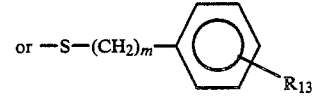

wherein m is zero, one, or two and $R_{13}$ is hydrogen, methyl, methoxy, methylthio, Cl, Br, F, or hydroxy, especially preferred wherein $R_7$ is hydrogen.

t is two or three, especially where t is two.

Preferred compounds of this invention with respect to the hydroxy substituted ureido portion of the structure of formula I are those wherein:

$R_1$ is straight or branched chain lower alkyl of 1 to 4 carbons, —CF$_3$, —(CH$_2$)$_2$—NH$_2$, —(CH$_2$)$_3$—NH$_2$, —(CH$_2$)$_4$—NH$_2$, —CH$_2$—OH,

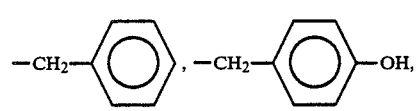

-continued

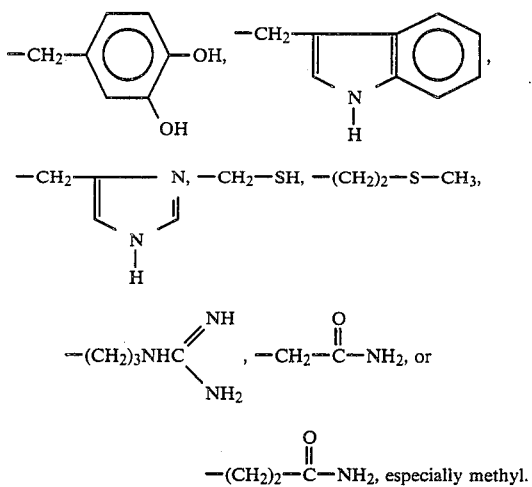

n is one.
R₂ is

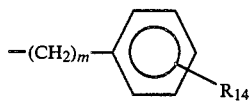

wherein m is zero, one, or two and R₁₄ is hydrogen, methyl, methoxy, methylthio, Cl, Br, F or hydroxy, especially phenyl.

R₃ is straight or branched chain lower alkyl of 1 to 4 carbons, —(CH₂)$_r$—NH₂,

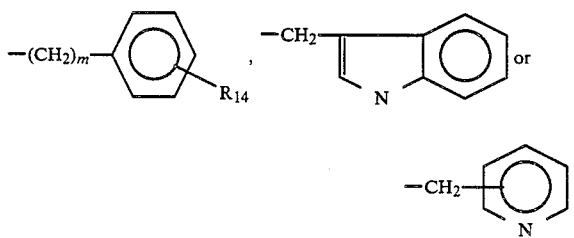

wherein m is zero, one, or two, R₁₄ is hydrogen, methyl, methoxy, methylthio, Cl, Br, F, or hydroxy, and r is an integer from 1 to 4, especially benzyl.

The compounds of formula I wherein R₆ is hydrogen form salts with a variety of inorganic or organic bases. The nontoxic, pharmaceutically acceptable salts are preferred, although other salts are also useful in isolating or purifying the product. Such pharmaceutically acceptable salts include metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

Similarly, the compounds of formula I, especially wherein R₆ is an ester group, form salts with a variety of inorganic and organic acids. Again, the non-toxic pharmaceutically acceptable salts are preferred, although other salts are also useful in isolating or purifying the product. Such pharmaceutically acceptable salts include those formed with hydrochloric acid, methanesulfonic acid, sulfuric acid, maleic acid, etc. The salts are obtained by reacting the product with an equivalent amount of the acid in a medium in which the salt precipitates.

As shown above, the amino or imino acid portion of the molecule of the products of formula I is in the L-configuration. One or two asymmetric centers are also present in the hydroxy substituted portion of the molecule as represented by the * in formula I. Of course, if R₃ is hydrogen, then only one center is present. Thus, the compounds of formula I can exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the R₇, R₈ and R₉ substituent in the starting material of formula XV.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg., preferably about 1 to 50 mg., per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methylclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

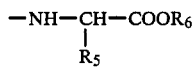

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade.

EXAMPLE 1

1-[[[(3S)-3-(Benzoylamino)-2-hydroxy-4-phenylbutyl]-methylamino]carbonyl]-L-proline(isomer A)

(a) (S)-3-Amino-1-chloro-4-phenyl-2-butanone, hydrogen bromide (S)-[3-Chloro-2-oxo-1-(phenylmethyl)propyl]carbamic acid, phenylmethyl ester (51.4 g.) is dissolved in a mixture of acetic acid (252 ml.) and hydrogen bromide in acetic acid (3.45N, 348 ml.) and kept at room temperature for 1.5 hours. The reaction mixture is then concentrated in vacuo and precipitated with ether to obtain 36.6 g. of (S)-3-amino-1-chloro-4-phenyl-2-butanone, hydrogen bromide; m.p. (175°) 177°–179°.

(b) (S)-N-[3-Chloro-2-oxo-1-(phenylmethyl)propyl]benzamide (S)-3-Amino-1-chloro-4-phenyl-2-butanone, hydrogen bromide (36.3 g., 130.3 mmole) is suspended in 520 ml. of dry tetrahydrofuran and 18.2 ml. of triethylamine (130.3 mmole) with stirring for ten minutes. The mixture is placed in an ice bath and 15.2 ml. of benzoyl chloride is added followed by 10.95 g. of sodium bicarbonate. After 5 minutes the ice bath is removed and the reaction mixture is kept at room temperature for 1.5 hours. The reaction mixture is then concentrated in vacuo and the residue taken up in 1 l. of aqueous methanol (10% water). The precipitate is collected, filtered and washed with methanol to obtain 25.3 g. of (S)-N-[3-chloro-2-oxo-1-(phenylmethyl)propyl]benzamide; m.p. (160°) 170°–172° (dec.); $[\alpha]_D^{23} = -129°$ (c=1.7, dimethylformamide).

(c) (S)-N-[3-[Methyl(phenylmethyl)amino]-2-oxo-1-phenylmethyl)propyl]benzamide

Benzylmethylamine (1.28 ml., 0.75 eq.) is added to a stirred suspension of (S)-N-[3-chloro-2-oxo-1-(phenylmethyl)propyl]benzamide (4.0 g., 13.2 mmole), sodium iodide (2.0 g., 2 eq.) and sodium bicarbonate (1.12 g., 1 eq.) in dry dimethylformamide (25 ml.) under argon. The resulting mixture is stirred at room temperature for 1.5 hours and then diluted with ether. After washing with water (twice), the organic phase is extracted with 0.5N hydrochloric acid (3×100 ml.). The hydrochloric acid fractions are combined and back extracted with ether and the organic fractions are discarded. The hydrochloric acid fraction is basified with sodium bicarbonate (20 g.) and extracted with ethyl acetate. The ethyl acetate fraction is washed with water and brine. After drying over anhydrous MgSO4, the solvent is removed at reduced pressure to give 2.46 g. of (S)-N-[3-[methyl(phenylmethyl)amino]-2-oxo-1-(phenylmethyl)-propyl]benzamide as a light yellow solid. TLC (silica gel, ethyl acetate) $R_f$=0.50.

(d) (S)-N-[3-(Methylamino)-2-oxo-1-(phenylmethyl)propyl]benzamide, hydrochloride A mixture of N-[3-[methyl(phenylmethyl)amino]-2-oxo-1-(phenylmethyl)propyl]benzamide (2.4 g., 6.32 mmole), 10 ml. of 1N hydrochloric acid (1.5 eq.) and palladium hydroxide on carbon catalyst (410 mg.) in 95% ethanol (90 ml.) is stirred under hydrogen (balloon). After stirring for 2 hours, the mixture is filtered (millipore) and the filtrate is concentrated at reduced pressure. The residue is chased once with absolute ethanol and the resulting material is washed with ether and dried under vacuum to give 1.95 g. of (S)-N-[3-(methylamino)-2-oxo-1-(phenylmethyl)propyl]benzamide, hydrochloride; $[\alpha]_D^{20} = -106.3°$ (c=1.04, methanol).

(e) 1-[[[(3S)-3-(Benzoylamino)-2-oxo-4-phenylbutyl]methylamino]carbonyl]-L-proline, phenylmethyl ester N-Methylmorpholine (0.60 ml., 2.5 eq.) is added to a stirred suspension of (S)-N-[3-methylamino)-2-oxo-1-(phenylmethyl)propyl]benzamide, hydrochloride (0.72 g., 2.16 mmole) in dry methylene chloride (11 ml.) at −20° under argon, followed by a 12.5% solution of phosgene in benzene (2.6 ml., 1.5 eq.). The resulting mixture is stirred at −20° for one hour and at room temperature for one hour. The solvent is then removed at reduced pressure and chased once with dry methylene chloride to remove the last traces of phosgene. The resulting residue is suspended in dry methylene chloride (15 ml.) and treated with L-proline, phenylmethyl ester, hydrochloride (0.55 g., 1.02 eq.) and N-methylmorpholine (0.60 ml., 2.5 eq.). After stirring at room temperature overnight, the mixture is diluted with ether and washed with water, 1N hydrochloric acid (twice), 1N sodium bicarbonate, and brine. After drying over anhydrous MgSO4, the solvent is removed at reduced pressure to give a yellow oil. This material is then redissolved in ether and allowed to stand overnight. The resulting precipitate is collected and washed with ether to give 597 mg. of 1-[[[(3S)-3-(benzoylamino)-2-oxo-4-phenylbutyl]methylamino]carbonyl]-L-proline, phenylmethyl ester as a colourless solid. TLC (silica gel; benzene:ethyl acetate; 6:4) $R_f$=0.22.

(f)
1-[[[(3S)-3-(Benzoylamino)-2-hydroxy-4-phenylbutyl]-methylamino]carbonyl]-L-proline, phenylmethyl ester (isomer A)

Sodium borohydride (154 mg., 4.08 mmole) is added to a solution of 1-[[[(3S)-3-(benzoylamino)-2-oxo-4-phenylbutyl]methylamino]carbonyl]-L-proline, phenylmethyl ester (720 mg., 1.36 mmole) in tetrahydrofuran (15 ml.) and water (3 ml.) at 0°. The resulting mixture is stirred at 0° for 10 minutes, the reaction is then quenched with 1N hydrochloric acid, diluted with ethyl acetate (approximately 150 ml.), and successively washed with 1N hydrochloric acid (twice), 1N sodium bicarbonate, and brine. After drying over anhydrous MgSO$_4$, the solvent is removed at reduced pressure to give a clear gummy oil as a mixture of diastereomers.

This material is flash chromatographed on silica gel (LPS-1, benzene:acetone; 4:1) to give 1-[[[(3S)-3-(benzoylamino)-2-hydroxy-4-phenylbutyl]methylamino]-carbonyl]-L-proline, phenylmethyl ester (isomer A) as a colorless solid. TLC (silica gel, benzene:acetone; 4:1) R$_f$=0.29.

(g)
1-[[[(3S)-3-(Benzoylamino)-2-hydroxy-4-phenylbutyl]-methylamino]carbonyl]-L-proline (isomer A)

A mixture of 1-[[[(3S)-3-(benzoylamino)-2-hydroxy-4-phenylbutyl]methylamino]carbonyl]-L-proline, phenylmethyl ester (isomer A) (790 mg., 149 mmole), palladium hydroxide on carbon catalyst (110 mg.) and ethanol: ethyl acetate (1:1, 20 ml.) is stirred under hydrogen gas (balloon) for one hour. The solution is filtered (millipore), and the solvent removed at reduced pressure to give the desired product as a colorless solid. Drying under vacuum over phosphorus pentoxide yields 569 mg. of 1-[[[(3S)-3-(benzoylamino)-2-hydroxy-4-phenylbutyl]methylamino]carbonyl]-L-proline (isomer A); m.p. 108°–117°; [α]$_D^{20}$= −77.5° (c=1.4, methanol). TLC (silica gel; chloroform:methanol:acetic acid; 18:1:1) R$_f$=0.39, trace at R$_f$=0.58.

Anal. calc'd for C$_{24}$H$_{29}$N$_3$O$_5$: C, 65.59; H, 6.65; N, 9.59. Found: C, 65.49; H, 6.99; N, 9.35.

EXAMPLE 2

1-[[[(3S)-3-(Benzoylamino)-2-hydroxy-4-phenylbutyl]-methylamino]carbonyl]-L-proline (isomer B)

(a)
1-[[[(3S)-3-(Benzoylamino)-2-hydroxy-4-phenylbutyl]-methylamino]carbonyl]-L-proline, phenylmethyl ester (isomer B)

The diastereomeric mixture from Example 1(f) is flash chromatographed on silica gel (LPS-1, benzene:acetone; 4:1) to give 0.59 g. of 1-[[[(3S)-3-(benzoylamino)-2-hydroxy-4-phenylbutyl]methylamino]-carbonyl]-L-proline, phenylmethyl ester (isomer B) as a colorless solid. TLC (silica gel; benzene:acetone; 4:1) R$_f$=0.16.

(b)
1-[[[(3S)-3-(Benzoylamino)-2-hydroxy-4-phenylbutyl]-methylamino]carbonyl]-L-proline (isomer B)

A mixture of 1-[[[(3S)-3-(benzoylamino)-2-hydroxy-4-phenyl]methylamino]carbonyl]-L-proline, phenylmethyl ester (isomer B) (230 mg., 0.433 mmole), palladium hydroxide on carbon catalyst (60 mg) in ethanol:ethyl acetate (1:1, 15 ml.) is stirred under hydrogen (balloon) for one hour. The solution is filtered (millipore), and the solvent removed at reduced pressure to give the desired product. This material is combined with that from a previous run and dried under vacuum over phosphorus pentoxide to give 273 mg. (85%) of 1-[[[(3S)-3-(benzoylamino)-2-hydroxy-4-phenylbutyl]-methylamino]carbonyl]-L-proline (isomer B) as a colorless solid; m.p. 118°–123°; [α]$_D^{20}$= −58.5° (c=1.0, methanol). TLC (silica gel; chloroform: methanol:acetic acid; 18:1:1) R$_f$=0.29, trace at R$_f$=0.53.

Anal. calc'd. for C$_{24}$H$_{29}$N$_3$O$_5$·0.42H$_2$O: C, 64.47; H, 6.72; N, 9.40. Found: C, 64.47; H, 6.52; N, 9.26.

EXAMPLE 3

(trans)-1-[[[(3S)-3-(Benzoylamino)-2-hydroxy-4-phenylbutyl]methylamino]carbonyl]-4-cyclohexyl-L-proline (a)
(trans)-1-[[[(3S)-3-(Benzoylamino)-2-oxo-4-phenylbutyl]methylamino]carbonyl]-4-cyclohexyl-L-proline, phenylmethyl ester N-Methylmorpholine (0.83 ml., 2.5 eq.) is added to a stirred suspension of (S)-N-[3-(methylamino)-2-oxo-1-(phenylmethyl)propyl]benzamide, hydrochloride (1.0 g., 3.0 mmole) in dry methylene chloride (15 ml.) at −20° under argon, followed by a 12.5% solution of phosgene in benzene (3.6 ml., 1.5 eq.). The resulting mixture is stirred at −20° for one hour then at room temperature for one hour. The solvent is then removed at reduced pressure and chased once with dry methylene chloride. The resulting mixture is suspended in 18 ml. of dry methylene chloride and treated with (trans)-4-cyclohexyl-L-proline, phenylmethyl ester (991 mg., 3.06 mmole) and N-methylmorpholine (0.83 ml., 2.5 eq.). After stirring overnight at room temperature, the mixture is diluted with ether and washed with water (twice), 1N hydrochloric acid (twice), 1N sodium bicarbonate, water, and brine. After drying over anhydrous MgSO$_4$ the solvent is removed at reduced pressure and the residue flash chromatographed on silica gel (LPS-1; benzene: ethyl acetate; 4:1) to give 1.08 g. of (trans)-1-[[[(3S)-3-(benzoylamino)-2-oxo-4-phenylbutyl]methylamino]carbonyl]-4-cyclohexyl-L-proline, phenylmethyl ester as a colorless foam. TLC (silica gel; benzene:ethyl acetate; 4:1) R$_f$=0.12.

(b)
(trans)-1-[[[(3S)-3-(Benzoylamino)-2-hydroxy-4-phenylbutyl]methylamino]carbonyl]-4-cyclohexyl-L-proline, phenylmethyl ester Sodium borohydride (62 mg., 2 eq.) is added to a stirred solution of (trans)-1-[[[(3S)-3-(benzoylamino)-2-oxo-4-phenylbutyl]methylamino]carbonyl]-4-cyclohexyl-L-proline, phenylmethyl ester (500 mg., 0.82 mmole) in 10 ml. of tetrahydrofuran and 2 ml. of water at 0°. The mixture is stirred at 0° for 15 minutes and then quenched with 1N hydrochloric acid and extracted with ethyl acetate. The ethyl acetate fraction is washed with water, 1N hydrochloric acid, 1N sodium bicarbonate, and brine. After drying over anhydrous MgSO$_4$, the solvent is removed at reduced pressure to give a white foam which is flash chromatographed on silica gel (LPS-1; benzene:ethyl acetate; 6:4) to give 460 mg. of (trans)-1-[[[(3S)-3-(benzoylamino)-2-hydroxy-4-phenylbutyl]methylamino]carbonyl]-4-cyclohexyl-L-proline, phenylmethyl ester as a colorless foam. TLC (silica gel; benzene:ethyl acetate) R$_f$=0.28.

(c)
(trans)-1-[[[(3S)-(Benzoylamino)-2-hydroxy-4-phenylbutyl]methylamino]carbonyl]-4-cyclohexyl-L-proline A solution of the diastereomeric ester product from part (b) (460 mg., 0.75 mmole), ethanol and ethyl acetate (1:1, 10 ml.), and 100% palladium hydroxide on carbon catalyst (100 mg.) is stirred under a hydrogen atmosphere (balloon). After stirring for one hour, the mixture is filtered (millipore) and the filtrate is concentrated at reduced pressure to give a gummy solid. Ether is added to this solid and then removed under vacuum to give 350 mg. of (trans)-1-[[[(3S)-3-(benzoylamino)-2-hydroxy-4-phenylbutyl]methylamino]carbonyl]-4-cyclohexyl-L-proline as a colorless solid; m.p. 131°–135°; $[\alpha]_D^{20} = -49.3°$ (c=0.28, methanol). TLC (silica gel; chloroform:acetic acid:methanol; 18:1:1) $R_f=0.46$.

Anal. calc'd. for $C_{30}H_{39}N_3O_5 \cdot 0.61 H_2O$: C, 67.63; H, 7.61; N, 7.89. Found: C, 67.63; H, 7.54; N, 7.57.

EXAMPLES 4–64

Following the procedures of Examples 1 to 3 the acylated alkylamine shown below in Col. I is treated with the acid chloride amino or imino acid ester of Col. II to give the ester compound shown in Col. III. Treatment with a reducing agent such as sodium borohydride followed by removal of the $R_6$ ester group yields the hydroxy substituted products shown in Col. IV.

| | Col. I $$R_3-CH-C-(CH_2)_n-NH \atop \underset{R_2}{\underset{|}{NH}} \underset{}{\overset{O}{\overset{\|}{C}}} \underset{}{\overset{R_1}{|}} \underset{}{\overset{O}{\|}}$$ | | | Col. II $$Cl-\overset{O}{\overset{\|}{C}}-X$$ | Col. III $$R_3-CH-C-(CH_2)_n-N-\overset{O}{\overset{\|}{C}}-X \atop \underset{C=O}{\underset{|}{NH}} \underset{R_2}{\underset{|}{}} \underset{R_1}{}$$ | Col. IV $$\underset{R_3-CH-CH-(CH_2)_n-N-\overset{O}{\overset{\|}{C}}-X}{\overset{OH}{|}} \atop \underset{C=O}{\underset{|}{NH}} \underset{R_2}{\underset{|}{}} \underset{R_1}{}$$ |
|---|---|---|---|---|---|---|
| Example | $R_1$ | n | $R_2$ | $R_3$ | | X |
| 4 | H₃C— | 2 | 4-CH₃-C₆H₄— | C₆H₅-CH₂— | | phenoxy-benzyl / COOCH₂Ph (L), H |
| 5 | H₅C₂— | 1 | 3-Cl-C₆H₄— | C₆H₅-CH₂— | | OH-benzyl / COOCH₂Ph (L), H |
| 6 | H₃C— | 1 | C₆H₅-CH₂— | H— | | OC(CH₃)₃-benzyl / COOCH₂Ph (L), H |
| 7 | F₃C— | 2 | C₆H₅-(CH₂)₂— | C₆H₅-CH₂— | | 4-F-C₆H₄-CH₂-benzyl / COOCH₂Ph (L), H |

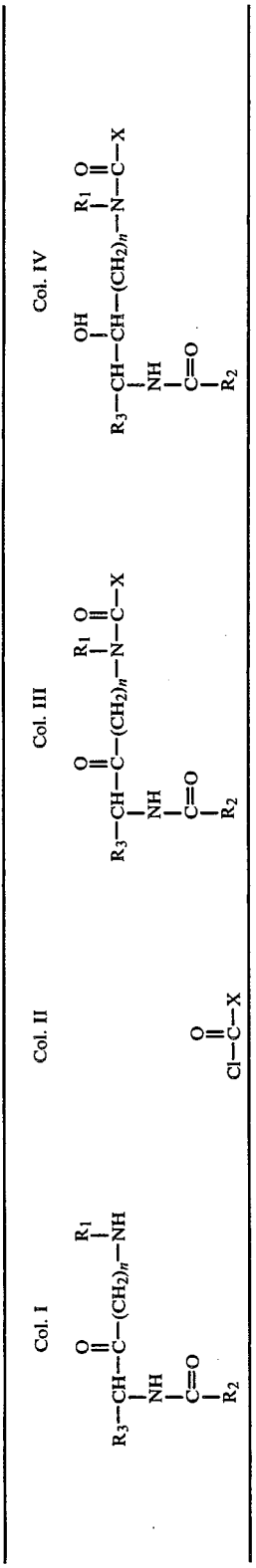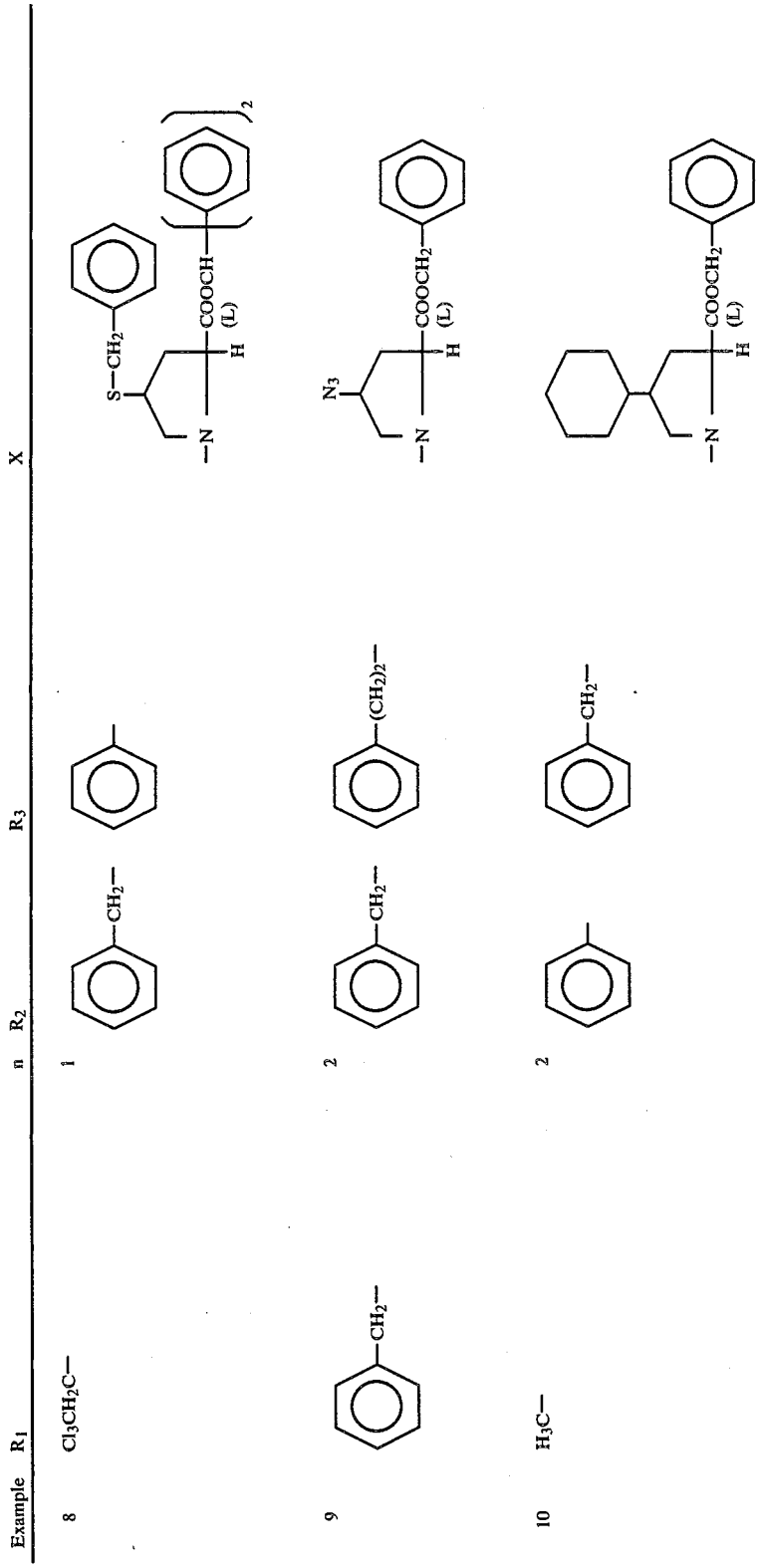

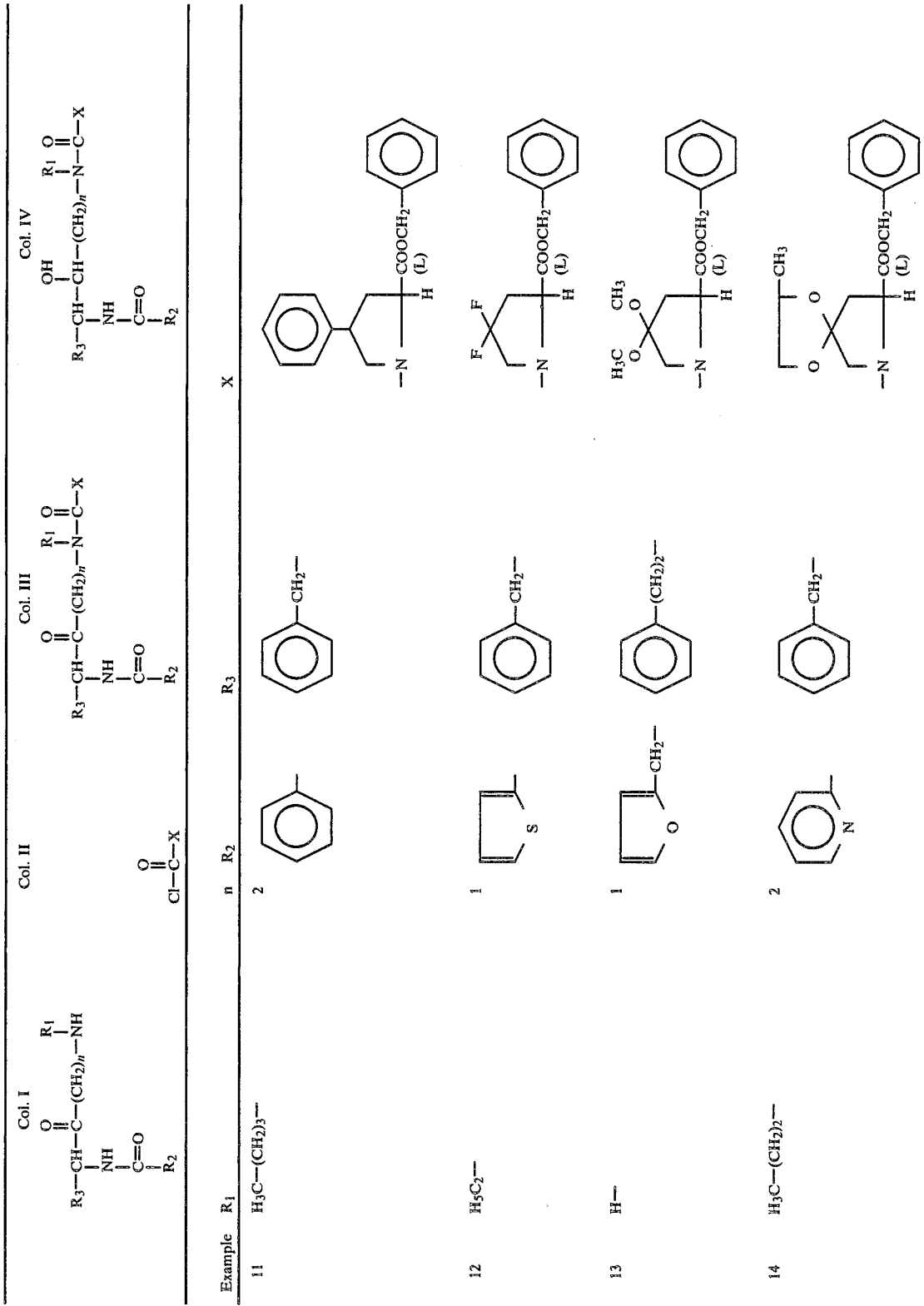

-continued

| | | Col. I<br>$R_3-CH-C-(CH_2)_n-NH$<br>$\|\quad\|\quad\quad\quad\|$<br>$NH\;\;O\quad\quad R_1$<br>$\|$<br>$C=O$<br>$\|$<br>$R_2$ | Col. II<br>$\quad O$<br>$\quad \|$<br>$Cl-C-X$ | | Col. III<br>$\quad\quad\quad\quad R_1\;\; O$<br>$\quad\quad\quad\quad \|\quad\|$<br>$R_3-CH-C-(CH_2)_n-N-C-X$<br>$\|\quad\quad\|$<br>$NH\;\;O$<br>$\|$<br>$C=O$<br>$\|$<br>$R_2$ | Col. IV<br>$\quad\quad\quad OH\quad R_1\;\;O$<br>$\quad\quad\quad\|\quad\quad\|\quad\|$<br>$R_3-CH-CH-CH-(CH_2)_n-N-C-X$<br>$\|$<br>$NH$<br>$\|$<br>$C=O$<br>$\|$<br>$R_2$ |
|---|---|---|---|---|---|---|
| Example | $R_1$ | | n | $R_2$ | $R_3$ | X |
| 15 | $H_3C-$ | | 1 | 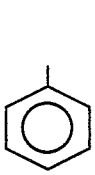 | 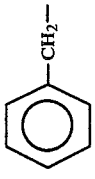 |  |
| 16 | $F_3C-$ | | 1 |  |  |  |
| 17 | $H_3C-$ | | 2 |  |  | 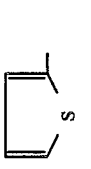 |
| 18 | $H_3C-$ | | 1 | 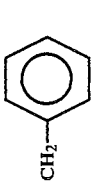 |  | 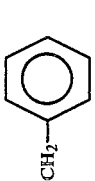 |

-continued

| | Col. I | Col. II | | Col. III | | Col. IV |
|---|---|---|---|---|---|---|
| | $R_3-CH-(CH_2)_n-NH$<br>$\quad\ \ \|\ \ R_1\ \ \|$<br>$\quad\ NH\quad C=O$<br>$\qquad\quad\ \ \|$<br>$\qquad\quad\ \ R_2$ | $Cl-C-X$<br>$\ \ \|\|$<br>$\ \ O$ | | $R_3-CH-C-(CH_2)_n-N-C-X$<br>$\quad\ \|\quad\ \|\|\qquad\qquad\ \|\ \ \|\|$<br>$\quad NH\ \ O\qquad\qquad R_1\ O$<br>$\quad\ \|$<br>$\quad C=O$<br>$\quad\ \|$<br>$\quad R_2$ | | $R_3-CH-CH-(CH_2)_n-N-C-X$<br>$\quad\ \|\quad\ \ \|\qquad\qquad\ \|\ \ \|\|$<br>$\quad NH\ OH\qquad\qquad R_1\ O$<br>$\quad\ \|$<br>$\quad C=O$<br>$\quad\ \|$<br>$\quad R_2$ |
| Example | $R_1$ | | n | $R_2$ | $R_3$ | X |
| 19 | 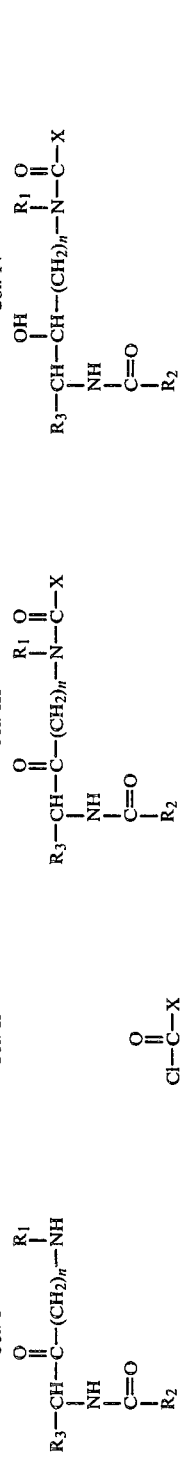 | | 1 |  |  |  |
| 20 |  | | 1 | $H_3C-$ | $H_3C-$ | 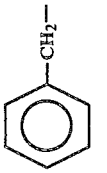 |
| 21 | $H_5C_2-$ | | 1 |  | $H_3C-$ |  |
| 22 | $H_3C-$ | | 1 | 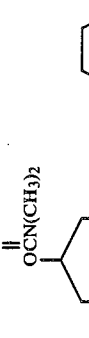 | $H_5C_2-$ | 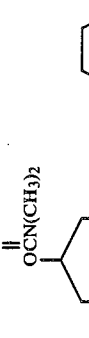 |

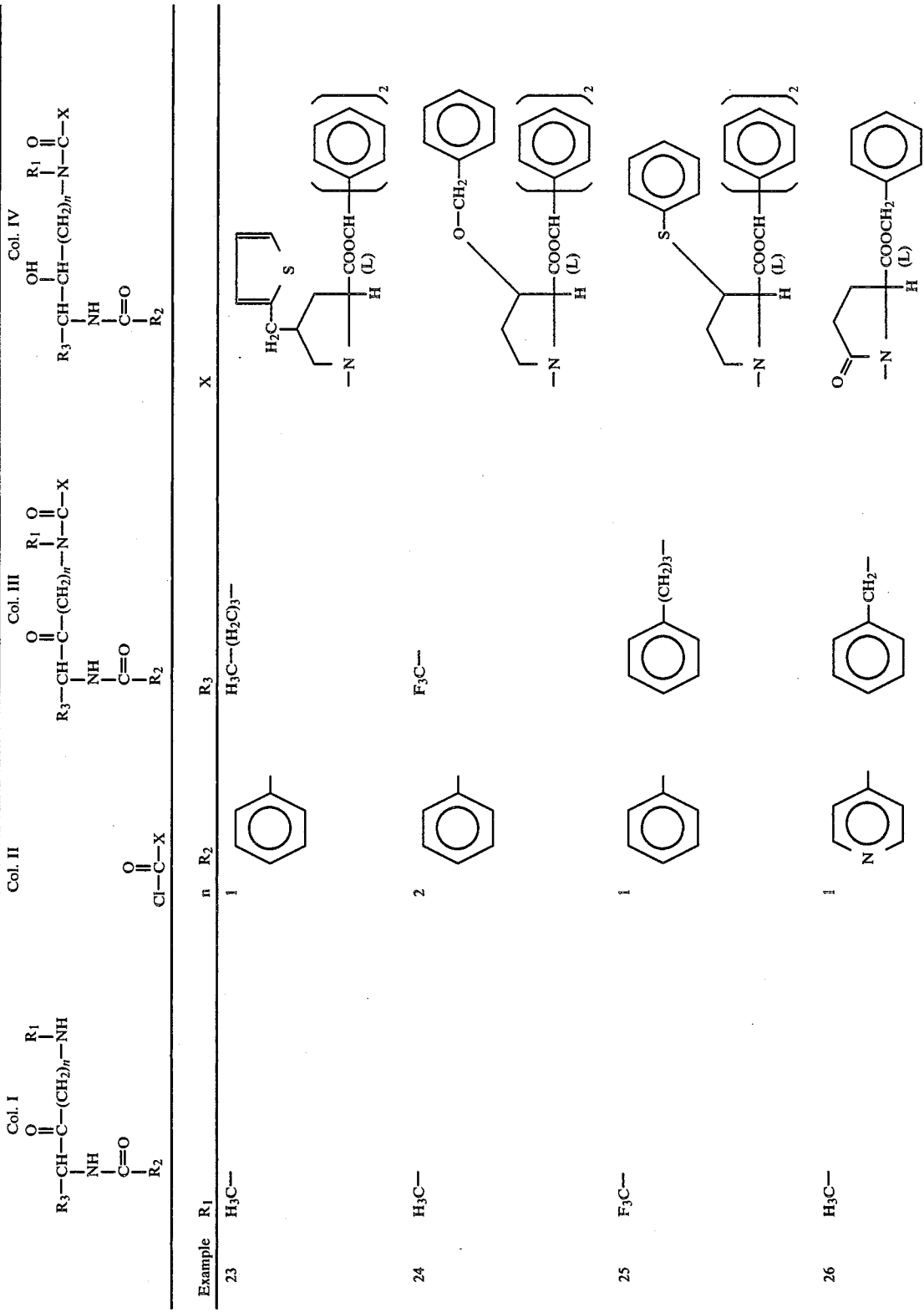

-continued

| | Col. I $R_3-CH-\underset{\underset{C=O}{\underset{|}{NH}}}{\overset{\overset{R_1}{\underset{|}{C}}-(CH_2)_n-NH}{\overset{O}{\|}}}$ $R_2$ | Col. II $\overset{O}{\underset{\|}{Cl-C-X}}$ | Col. III $R_3-CH-\overset{O}{\underset{\|}{C}}-\overset{R_1}{\underset{|}{C}}-(CH_2)_n-\overset{O}{\underset{\|}{N-C-X}}$ $\underset{\underset{C=O}{\underset{|}{NH}}}{}$ $R_2$ | Col. IV $R_3-CH-\overset{O}{\underset{\|}{C}}-\overset{R_1}{\underset{|}{C}}-(CH_2)_n-\overset{O}{\underset{\|}{N-C-X}}$ $\underset{\underset{C=O}{\underset{|}{NH}}}{}$ $R_2$ |
|---|---|---|---|---|
| Example | $R_1$ | n $R_2$ | $R_3$ | X |
| 27 | $H_5C_2-$ | 2 ![phenyl-(CH_2)_3-] | ![phenyl] | ![benzyl-OH-CH-CH_2-N(COOCH_2Ph)(L)H] |
| 28 | $H_3C-$ | 2 ![phenyl] | ![phenyl-(CH_2)_4-] | ![thiazolidine-N-COOCH_2(Ph)_2(L)H] |
| 29 | $H_3C-$ | 1 ![phenyl] | ![phenyl-(CH_2)_3-] | ![dehydroproline-N-COOCH_2Ph(L)H] |
| 30 | $H_3C-$ | 1 ![phenyl] | ![H_3CS-phenyl-CH_2-] | ![piperidine-N-COOCH_2(Ph)_2(L)H] |
| 31 | $H_5C_2-$ | 2 ![thiophene] | ![phenyl-CH_2-] | ![proline-N-COOCH_2Ph(L)H] |

-continued

| | Col. I<br>$R_3-CH-(CH_2)_n-NH$<br>$\|$ $\|$<br>$NH$ $R_1$<br>$\|$<br>$C=O$<br>$\|$<br>$R_2$ | | Col. II<br>O<br>$\|\|$<br>Cl—C—X | Col. III<br>$R_1$ O<br>$\|$ $\|\|$<br>$R_3-CH-C-(CH_2)_n-N-C-X$<br>$\|$<br>$NH$<br>$\|$<br>$C=O$<br>$\|$<br>$R_2$ | Col. IV<br>OH $R_1$ O<br>$\|$ $\|$ $\|\|$<br>$R_3-CH-CH-CH-(CH_2)_n-N-C-X$<br>$\|$<br>$NH$<br>$\|$<br>$C=O$<br>$\|$<br>$R_2$ |
|---|---|---|---|---|---|
| Example | $R_1$ | n | $R_2$ | $R_3$ | X |
| 32 | $H_3C-$ | 2 | 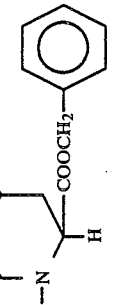 | 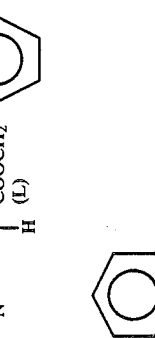 |  |
| 33 | $H_5C_2-$ | 1 |  | 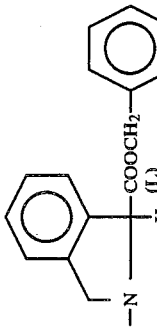 | 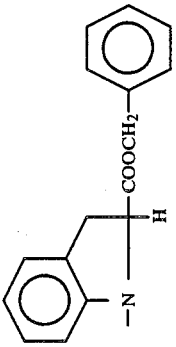 |
| 34 | $H_3C-$ | 2 |  |  | 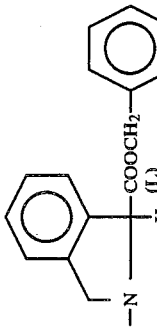 |
| 35 | $\begin{array}{c}HN\\ \|\|\\ O_2N-NH\end{array}C-HN-(H_2C)_3-$ | 1 | 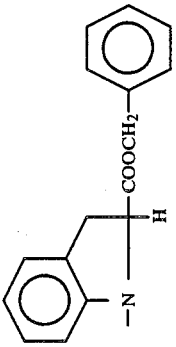 |  | 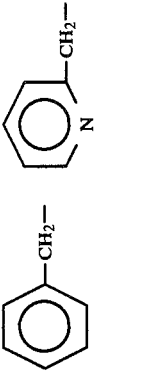 |

-continued

| Example | Col. I R₁ | n | R₂ | Col. III R₃ | Col. IV X |
|---|---|---|---|---|---|
| 36 | H₂COCHN(H₂C)₄— with phenyl and C=O | 2 | phenyl | PhCH₂— | -N(CH₂-S-C(CH₃)₂-S-CH₂-)CH(COOCH₂Ph)(L), H (dithiolane structure) |
| 37 | 4-PhOCH₂-C₆H₄-CH₂— | 1 | phenyl | PhCH₂— | -N-CH(cyclohexylmethyl)CH(COOCH₂Ph)(L), H |
| 38 | 3,4-bis(PhOCH₂)-C₆H₃-CH₂— | 1 | thienyl | Ph(CH₂)₂— | -N-CH(propyl)CH(COOCH₂Ph)(L), H |
| 39 | indol-2-yl-CH₂— | 2 | pyridyl | PhCH₂— | -N-CH(propyl)CH(COOCH₂Ph)(L), H |

-continued

| Example | Col. I $R_1$ | n | $R_2$ | Col. III $R_3$ | Col. IV X |
|---|---|---|---|---|---|
| 40 | (N-CH=CH-CH₂ group with N-CH₂-phenyl) | 1 | phenyl | thiophene-CH₂– | tetrahydroisoquinoline-COOCH₂-phenyl (L) |
| 41 | H₂COCHN–(H₂C)₄– (with phenyl) | 1 | phenyl | phenyl-CH₂– | piperidine-COOCH₂-phenyl (L) |
| 42 | H₃C– | 1 | phenyl | HN=C(NH-NO₂)–HN–(H₂C)₃– | piperidine-COOCH₂-phenyl (L) |
| 43 | H₃C– | 1 | phenyl | (3,4-bis(benzyloxy)benzyl, H₂CO- and H₂CO- substituents) | piperidine-COOCH₂-phenyl (L) |

-continued

| Example | Col. I $R_3-CH(NH-C(=O)-R_2)-C(=O)-(CH_2)_n-NH-R_1$ | | | Col. II $Cl-C(=O)-X$ | Col. III $R_3-CH(NH-C(=O)-R_2)-C(=O)-(CH_2)_n-N(R_1)-C(=O)-X$ | Col. IV $R_3-CH(NH-C(=O)-R_2)-CH(OH)-(CH_2)_n-N(R_1)-C(=O)-X$ |
|---|---|---|---|---|---|---|
| | $R_1$ | n | $R_2$ | $R_3$ | | X |
| 44 | H₃C— | 1 | phenyl | 3-indolyl-CH₂— | | thiazolidine-proline-CH(COOCH(phenyl)₂)(L) |
| 45 | H₃C— | 1 | phenyl | benzyl (PhCH₂—) | | —NH—CH₂—COOCH₂—phenyl |
| 46 | F₃C— | 2 | 2-pyridyl | Ph(CH₂)₄— | | —NH—CH(CH₃)—COOCH₂—phenyl (L) |
| 47 | benzyl (PhCH₂—) | 1 | phenyl | H— | | —NH—CH(CH₂CH(CH₃)₂)—COOCH₂—phenyl (L) |

-continued

| | Col. I | Col. II | Col. III | | | Col. IV |
|---|---|---|---|---|---|---|
| | $$R_3-\overset{\underset{\displaystyle NH}{\mid}}{CH}-\overset{O}{\overset{\|}{C}}-(CH_2)_n-\overset{R_1}{\overset{\mid}{N}}H \\ \overset{\|}{\underset{R_2}{C=O}}$$ | $$\overset{O}{\overset{\|}{Cl-C}}-X$$ | $$R_3-\overset{\underset{\displaystyle NH}{\mid}}{CH}-\overset{O}{\overset{\|}{C}}-(CH_2)_n-\overset{R_1}{\overset{\mid}{N}}-\overset{O}{\overset{\|}{C}}-X \\ \overset{\|}{\underset{R_2}{C=O}}$$ | | | $$R_3-\overset{\underset{\displaystyle NH}{\mid}}{CH}-\overset{OH}{\overset{\mid}{CH}}-(CH_2)_n-\overset{R_1}{\overset{\mid}{N}}-\overset{O}{\overset{\|}{C}}-X \\ \overset{\|}{\underset{R_2}{C=O}}$$ |
| Example | $R_1$ | | n | $R_2$ | $R_3$ | X |
| 48 | $H_5C_2-$ | | 1 | 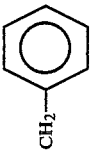 | 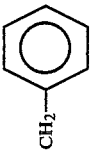 | 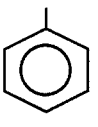 |
| 49 | $H_3C-$ | | 1 | 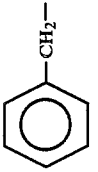 | 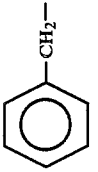 | 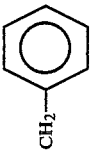 |

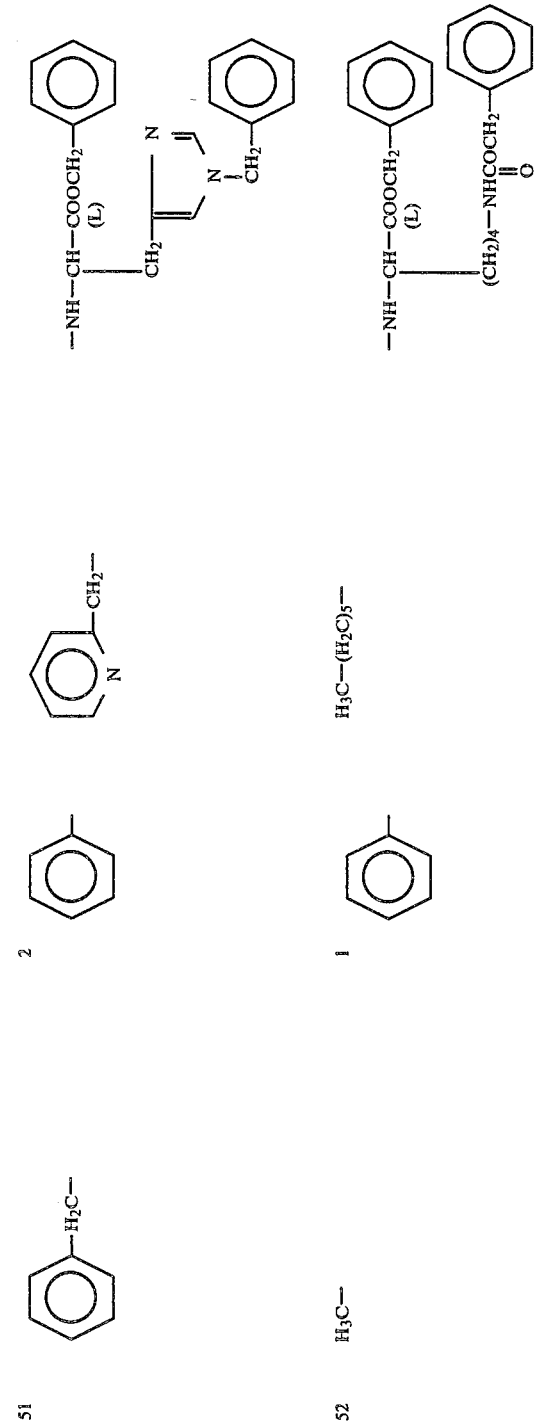

-continued

| | Col. I<br>$R_3-CH-C-(CH_2)_n-NH$<br>$\quad\quad\|\quad\quad\|\quad\quad\|$<br>$\quad\quad NH\quad O\quad R_1$<br>$\quad\quad\|$<br>$\quad\quad C=O$<br>$\quad\quad\|$<br>$\quad\quad R_2$ | Col. II<br>$\overset{O}{\underset{\|}{Cl-C-X}}$ | Col. III<br>$R_3-CH-C-(CH_2)_n-N-C-X$<br>$\quad\quad\|\quad\quad\|\quad\quad\quad\quad\|\quad\|$<br>$\quad\quad NH\quad O\quad\quad\quad R_1\, O$<br>$\quad\quad\|$<br>$\quad\quad C=O$<br>$\quad\quad\|$<br>$\quad\quad R_2$ | | | Col. IV<br>$\quad\quad OH\quad R_1\, O$<br>$\quad\quad\|\quad\quad\|\quad\|$<br>$R_3-CH-CH-(CH_2)_n-N-C-X$<br>$\quad\quad\|$<br>$\quad\quad NH$<br>$\quad\quad\|$<br>$\quad\quad C=O$<br>$\quad\quad\|$<br>$\quad\quad R_2$ |
|---|---|---|---|---|---|
| Example | $R_1$ | | n | $R_2$ | $R_3$ | X |
| 53 | $H_3C-$ | | 1 | phenyl | 2,3-dihydrothiophen-yl | $-NH-CH-COOCH_2-(phenyl)_2$ (L), $CH_2-S-CH_2$ linker with another phenyl |
| 54 | $H_5C_2-$ | | 1 | benzyl | benzyl | $-NH-CH-COOCH_2-phenyl$ (L), $(CH_2)_3NHC(=NH)NHNO_2$ |
| 55 | $H_3C-$ | | 2 | phenyl | benzyl | $-NH-CH-COOCH_2-phenyl$ (L), $(CH_2)_2-C(=O)-NH_2$ |

| | Col. I | Col. II | | | Col. III | Col. IV |
|---|---|---|---|---|---|---|
| | $R_3-CH-C-(CH_2)_n-NH$ with $R_1$, NH, C=O, $R_2$ | Cl—C—X | | | $R_3-CH-C-(CH_2)_n-N-C-X$ with $R_1$, NH, C=O, $R_2$ | $R_3-CH-CH-(CH_2)_n-N-C-X$ with OH, $R_1$, NH, C=O, $R_2$ |
| Example | $R_1$ | n | $R_2$ | $R_3$ | | X |
| 56 | H₃C— | 1 | —CH₂—C₆H₅ | —C₆H₅ | | phenacyl hydrazone with —COOCH₂C₆H₅ (L) |
| 57 | H₃C— | 1 | —CH₂—C₆H₅ | —C₆H₅ | | —N(C₆H₅)—CH₂—COOCH₂C₆H₅ |
| 58 | H₃C— | 2 | —CH₂—C₆H₅ | —C₆H₅ | | —N(C₆H₁₁)—CH₂—COOCH₂C₆H₅ |
| 59 | H₃C— | 1 | —CH₂—C₆H₅ | —CH₂—C₆H₅ | | pyrrolidine-type with —CH(C₆H₁₁)—O—C(=O)—OC₂H₅ (L) |

-continued
| | Col. I<br>R$_3$—CH—C—(CH$_2$)$_n$—NH<br>   \|        \|<br>   NH       R$_1$<br>   \|<br>   C=O<br>   \|<br>   R$_2$ | Col. II<br>O<br>\|\|<br>Cl—C—X | | Col. III<br>R$_3$—CH—C—(CH$_2$)$_n$—N—C—X<br>   \|              \|  \|\|<br>   NH             R$_1$ O<br>   \|<br>   C=O<br>   \|<br>   R$_2$ | Col. IV<br>OH R$_1$ O<br>\|   \|   \|\|<br>R$_3$—CH—CH—(CH$_2$)$_n$—N—C—X<br>   \|<br>   NH<br>   \|<br>   C=O<br>   \|<br>   R$_2$ |
|---|---|---|---|---|---|
| Example | R$_1$ | n | R$_2$ | R$_3$ | X |
| 60 | H$_3$C— | 1 |  | 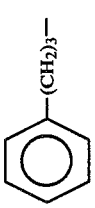 | 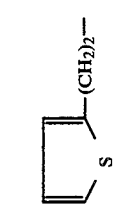 |
| 61 | H$_3$C— | 2 | 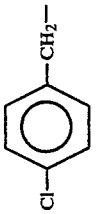 | 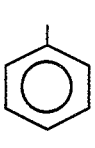 | 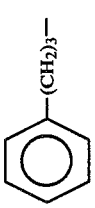 |
| 62 | F$_3$C— | 1 | 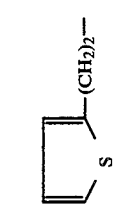 | 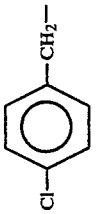 | 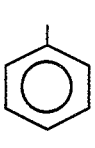 |
| 63 | H$_3$C— | 1 | 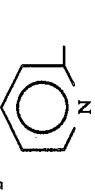 |  |  |
| 64 | H$_3$C—(H$_2$C)$_3$— | 2 | 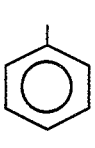 | 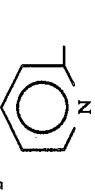 |  |

The R₁ protecting groups in Examples 19, 35 to 38, 40 and 41, the R₃ protecting groups in Examples 42 and 43, and the R₅ protecting groups in Examples 48, 49, and 51 to 54 are removed as the last step in the synthesis. The R₆ ester groups shown in Examples 59 to 64 are not removed.

EXAMPLE 65

(±)-1-[[[4-(Benzoylamino)-3-hydroxy-5-phenylpentyl]methylamino]carbonyl]-L-proline (a) 3-(Methylamino)propanoic acid, methyl ester Methyl amine (66 ml.) in ethanol is chilled with stirring in an ice-bath. Methyl acrylate (45 ml.) is added dropwise over a period of 20 minutes. The bath is removed after one hour and after 4 hours the reaction mixture is concentrated in vacuo. The liquid is distilled at 15 mm. of Hg. at 61°–63° to give 18 g. of 3-(methylamino)propanoic acid, methyl ester.

(b) 1-[[(3-Methoxy-3-oxopropyl)methylamino]carbonyl]-L-proline, 1,1-dimethylethyl ester L-Proline, 1,1-dimethylethyl ester (8.55 g.) is taken up into 200 ml. of methylene chloride with stirring at −20°. A solution of phosgene in benzene (12.5% by weight, 60 ml.) is added followed by 8.25 ml. of N-methylmorpholine. After 30 minutes at −20° the reaction mixture is concentrated in vacuo. The residue is taken up into 100 ml. of methylene chloride with stirring in an ice-bath. To this 7.0 g. of 3-(methylamino)propanoic acid, methyl ester is added followed by N-methyl morpholine (5.5 ml.). After one hour the ice-bath is removed and the reaction mixture is kept at room temperature overnight. The reaction mixture is then concentrated in vacuo, taken up into ethyl acetate and washed with 10% potassium bisulfate and saturated sodium bicarbonate to yield 14.9 g. of crude product. Crystallization from ether/hexane yields 10.7 g. of 1-[[(3-methoxy-3-oxopropyl)methylamino]carbonyl]-L-proline, 1,1-dimethylethyl ester; m.p. 70°–71°.

(c) 1-[[(2-Carboxyethyl)methylamino]carbonyl]-L-proline, 1,1-dimethylethyl ester 1-[[(3-Methoxy-3-oxopropyl)methylamino]carbonyl]-L-proline, 1,1-dimethylethyl ester (7.2 g.) is taken up into 47.7 ml. of methanol to which 28.6 ml. of 1N sodium hydroxide is added with stirring. After 2.5 hours the methanol is removed in vacuo. The aqueous phase is acidified with dilute hydrochloric acid and extracted into ethyl acetate to give 7.1 g. of crude product. Crystallization from ether/hexane yields 6.1 g. of 1-[[(2-carboxyethyl)methylamino]carbonyl]-L-proline, 1,1-dimethylethyl ester; m.p. 69°–71°.

(d) (±)-1-[[[4-(Benzoylamino)-3-oxo-5-phenylpentyl]methylamino]carbonyl]-L-proline, 1,1-dimethylethyl ester 1-[[(2-Carboxyethyl)methylamino]carbonyl]-L-proline, 1,1-dimethylethyl ester (900 mg.) is taken up into 10.5 ml. of tetrahydrofuran with stirring in an ice-bath. To this oxalyl chloride (0.3 ml.) is added followed by 2 drops of dimethylformamide. After 20 minutes the ice-bath is removed. After one hour at room temperature the reaction mixture is concentrated to dryness in vacuo. The residue is taken up into 6 ml. of tetrahydrofuran and while stirring in an ice-bath 2-phenyl-4-(phenylmethyl)-5(4H)-oxazolone (754 mg.) in 4.8 ml. of tetrahydrofuran is added dropwise followed by triethylamine (0.42 ml.). The reaction mixture is kept at room temperature overnight, the triethylamine hydrochloride salt is filtered off and the filtrate is concentrated to dryness. The residue is taken up into 3.0 ml. of pyridine and stirred for 3 hours with 9 mg. of 4-dimethylamino pyridine. Acetic acid (3 ml.) is added and the mixture is heated at 100°–105° for 30 minutes, concentrated in vacuo, taken up into ethyl acetate and washed with saturated sodium bicarbonate and dilute hydrochloric acid to yield 1.1 g. of crude product. Purification on a silica gel column eluting with ethyl acetate: hexane (2:1) gives 330 mg of (±)-1-[[[4-(benzoylamino)-3-oxo-5-phenylpentyl]methylamino]carbonyl]-L-proline, 1,1-dimethylethyl ester.

(e) (±)-1-[[[4-(Benzolylamino)-3-oxo-5-phenylpentyl]methylamino]carbonyl]-L-proline The t-butyl ester product from part (d) (300 mg.) is treated for 1.5 hours with 3 ml. of trifluoroacetic acid, concentrated in vacuo and triturated to a solid with ether/hexane to give 250 mg. of (±)-1-[[[4-(benzoylamino)-3-oxo-5-phenylpentyl]methylamino]carbonyl]-L-proline, m.p. 38°–68°; $[\alpha]_D^{23} = -9.16°$ (c=1.2, methanol); $R_f$=0.71 [silica gel, chloroform:methanol:acetic acid (9:0.5:0.5)].

Anal. calc'd. for $C_{25}H_{29}N_3O_5 \cdot 1.37\ H_2O$: C, 63.04; H, 6.72; N, 8.82. Found: C, 63.04; H, 6.29; N, 8.61.

(f) (±)-1-[[[4-(Benzoylamino)-3-hydroxy-5-phenylpentyl]methylamino]carbonyl]-L-proline The product from part (e) is treated with sodium borohydride according to the procedure of Example 1(f) to yield (±)-1-[[[4-(benzoylamino)-3-hydroxy-5-phenylpentyl]methylamino]carbonyl]-L-proline.

EXAMPLE 66

(±)-1-[[[3-(Benzoylamino)-2-hydroxyheptyl]methylamino]carbonyl]-L-proline (a) N-[(Phenylmethoxy)carbonyl]sarcosine, 1,1-dimethylethyl ester A solution of N-[(phenylmethoxy)carbonyl]sarcosine (114.5 g.), methylene chloride (250 ml.), concentrated sulfuric acid (4 ml.) and isobutylene (600 ml.) is shaken in a Parr shaker for 3 days followed by neutral wash to give 136.5 g. of N-[(phenylmethoxy)carbonyl]-sarcosine, 1,1-dimethylethyl ester.

(b) Sarcosine, 1,1-dimethylethyl ester

N-[(Phenylmethoxy)carbonyl]-sarcosine, 1,1-dimethylethyl ester (68 g., 238 mmole) is taken into absolute ethanol (500 ml.) and stirred under hydrogen in the presence of 10% palladium on carbon catalyst (6.6 g.) overnight at room temperature. The reaction mixture is then filtered to remove the catalyst and concentrated in vacuo to remove the ethanol and give 20.6 g. of sarcosine, 1,1-dimethylethyl ester as an oil.

(c) 1-[[N-[[(1,1-Dimethylethoxy)carbonyl]methyl]methylamino]carbonyl]-L-proline, phenylmethyl ester L-Proline, phenylmethyl ester, hydrochloride (2.41 g., 10 mmole) is taken into 40 ml. of methylene chloride and N-methylmorpholine (2.8 ml., 25 mmole) with stirring at −20°. To this is added dropwise 12.5% phosgene in benzene (16 ml., 15 mmole). After 30 minutes at −20°, the mixture is concentrated to dryness in vacuo and taken into 40 ml. of methylene chloride with stirring in an ice bath. To this is added sarcosine, 1,1-dimethylethyl ester (1.6 g., 11 mmole) followed by N-methylmorpholine (1.1 ml., 10 mmole). After one hour the bath is removed and the reaction mixture is stirred overnight at room temperature, concentrated in vacuo, taken into ethyl acetate and washed neutral with 10% potassium bisulfate and saturated sodium bicarbonate. The crude residue (3.6 g.) is purified in 180 g. of silica gel in ethyl acetate:hexane (1:1) to give 2.7 g. of 1-[[N-[[(1,1-dimethylethoxy)carbonyl]methyl]methylamino]-carbonyl]-L-proline, phenylmethyl ester.

(d)
1-[[(2-Carboxyethyl)methylamino]carbonyl]-L-proline, phenylmethyl ester

The ester product from part (c) (2.7 g., 7.17 mmole) is treated for 1.5 hours with 10 ml. of trifluoroacetic acid and 1.6 ml. of anisole. After concentrating to dryness it is triturated with ether-hexane. The crude material is crystallized from ether to yield 2 g. of 1-[[(2-carboxyethyl)methylamino]carbonyl]-L-proline, phenylmethyl ester; m.p. 102°-104°.

(e) N-(Benzoyl)-D,L-norleucine

D,L-Norleucine (39.3 g., 300 mmole) is taken into 150 ml. of 2N sodium hydroxide and while stirring in an ice bath 150 ml. of 2N sodium hydroxide and benzoyl chloride (38.3 ml., 330 mmole) are added over a 30 minute period. The bath is removed and after 1.5 hours the reaction mixture is extracted with ether. The aqueous portion is acidified with 2N hydrochloric acid and the crystals filtered to give 68.9 g. of N-(benzoyl)-D,L-norleucine; m.p. (125) 131°-133°.

(f) 2-Phenyl-4-butyl-5(4H)-oxazolone

N-(Benzoyl)-D,L-norleucine (40 g., 170 mmole) is taken into 300 ml. of tetrahydrofuran with stirring in an ice bath. To this is added dropwise dicyclohexylcarbodiimide (38.52 g., 187 mmole) in tetrahydrofuran (195 ml.). After 15 minutes the bath is removed and the reaction is allowed to run overnight. The dicyclohexylurea is filtered off and the filtrate is concentrated to dryness. The crude product (31.7 g.) is purified on silica gel in hexane:ether (2:1) to give 2-phenyl-4-butyl-5(4H)-oxazolone. This product crystallizes neat when refrigerated.

(g)
(±)-1-[[[3-(Benzoylamino)-2-oxoheptyl]methylamino]-carbonyl]-L-proline, phenylmethyl ester 1-[[(2-Carboxyethyl)methylamino]carbonyl]-L-proline, phenylmethyl ester (4.8 g., 15 mmole) is taken into 50 ml. of dry tetrahydrofuran with stirring in an ice bath. To this is added dropwise oxalyl chloride (1.58 ml., 18 mmole) followed by 4 drops of dimethylformamide. After 20 minutes the bath is removed and the reaction is run for one hour at room temperature before concentrating to dryness. This material is taken into 30 ml. of tetrahydrofuran, chilled and added dropwise to 2-phenyl-4-butyl-5(4H)-oxazolone (3.42 g., 15.75 mmole) in 24 ml. of tetrahydrofuran while stirring in an ice bath. Triethylamine (2.55 ml.) is added. After 5 minutes the bath is removed and the reaction is run overnight at room temperature. The triethylamine hydrochloride salt is filtered off, the filtrate is concentrated to dryness, taken into 16 ml. of pyridine, 50 mg. of 4-dimethylamino pyridine is added, and the mixture is stirred for 3 hours. Acetic acid (16 ml.) is added and the mixture is heated at 100° for 45 minutes. The mixture is concentrated to dryness, taken into ethyl acetate and washed neutral with saturated sodium bicarbonate and dilute hydrochloric acid to give 4.7 g. of product. Purification on silica gel in benzene:ethyl acetate (1:2) yields 1.14 g. of (±)-1-[[[3-(benzoylamino)-2-oxoheptyl]methylamino]carbonyl]-L-proline, phenylmethyl ester.

(h)
(±)-1-[[[3-(Benzoylamino)-2-oxoheptyl]methylamino]-carbonyl]-L-proline

The ester product from part (g) (650 mg.) is taken into 30 ml. of absolute ethanol containing 120 mg. of 10% palladium on carbon catalyst and reduced under hydrogen for 20 hours. The reaction mixture is filtered and concentrated to dryness to yield 500 mg. crude product. Purification on a silica gel column with chloroform:methanol:acetic acid (90:5:5) gives 340 mg. of (±)-1-[[[3-(benzoylamino)-2-oxoheptyl]methylamino]carbonyl]-L-proline; m.p. 40°-80°; $[\alpha]_D^{23} = -8.2°$ (c=1.1, methanol). $R_f$ 0.52 (silica gel; chloroform:methanol:acetic acid; 90:5:5).

Anal. calc'd. for $C_{21}H_{29}N_3O_5 \cdot 0.86\ H_2O$: C, 60.19; H, 7.39; N, 10.03. Found: C, 60.19; H, 7.13; N, 10.34.

(i)
(±)-1-[[[3-(Benzoylamino)-2-hydroxyheptyl]methylamino]carbonyl]-L-proline

The product from part (h) is treated with sodium borohydride according to the procedure of Example 1(f) to yield (±)-1-[[[3-(benzoylamino)-2-hydroxyheptyl]methylamino]carbonyl]-L-proline.

EXAMPLE 67

(±)-1-[[[7-Amino-3-(benzoylamino)-2-hydroxyheptyl]-methylamino]carbonyl]-L-proline (a)
$N^2$-Benzoyl-$N^6$-[(phenylmethoxy)carbonyl]-L-lysine $N^6$-[(Phenylmethoxy)carbonyl]-L-lysine (20.18 g., 72 mmole) is taken into 72 ml. of 1N sodium hydroxide with stirring in an ice bath. To this over 20 minutes is added benzoyl chloride (10.0 ml., 86.2 mmole) and 4N sodium hydroxide (21.6 ml.). The bath is removed and the reaction is allowed to run for 1.5 hours at room temperature. The mixture is extracted with ethyl acetate, the aqueous portion is acidified with dilute hydrochloric acid, and extracted with ethyl acetate. The ethyl acetate extract is concentrated to low volume and hexane is added to crystallize out 25.7 g. of $N^2$-benzoyl-$N^6$-[(phenylmethoxy)carbonyl]-L-lysine; m.p. 110°-112°.

(b)
2-Phenyl-4-[[(phenylmethoxy)carbonyl]amino]-butyl]-5(4H)-oxazolone $N^2$-Benzoyl-$N^6$-[(phenylmethoxy)carbonyl]-L-lysine (23.06 g., 60 mmole) is taken into 110 ml. of dry tetrahydrofuran with stirring in an ice bath. To this dicyclohexylcarbodiimide (13.6 g., 66 mmole) is added dropwise in 70 ml. of dry tetrahydrofuran. The bath is removed and the reaction is kept at room temperature overnight. The dicyclohexylurea is filtered off and the filtrate is concentrated to dryness and crystallized from ethyl acetate:hexane to give 21.4 g. of 2-phenyl-4-[4-[[(phenylmethoxy)carbonyl]amino]butyl]-5(4H)-oxazolone.

(c) (±)-1-[[[3-(Benzoylamino)-7-[[(phenylmethoxy)carbonyl]amino]-2-oxoheptyl]methylamino]carbonyl]-L-proline, phenylmethyl ester 1-[[(2-Carboxyethyl)methylamino]carbonyl]-L-proline, phenylmethyl ester (6.4 g., 20 mmole) is taken into 65 ml. of dry tetrahydrofuran with stirring in an ice bath. Oxalyl chloride (2.1 ml., 24 mmole) is added dropwise followed by 5 drops of dimethylformamide. After 20 minutes the ice bath is removed. After one hour at room temperature the reaction mixture is concentrated to dryness in vacuo. The residue is taken into 40 ml. of dry tetrahydrofuran and added dropwise to $N^2$-benzoyl-$N^6$-[(phenylmethoxy)carbonyl]-L-lysine (7.7 g., 24 mmole) in 30 ml. of dry tetrahydrofuran while stirring in an ice bath. Triethylamine (3.4 ml., 24 mmole) is then added. The reaction is run overnight at room temperature. The triethylamine hydrochloride salt is filtered off, the filtrate is concentrated to dryness, taken into pyridine (21.2 ml.), 4-dimethylamino pyridine (66.6 mg.) is added, and the mixture is stirred for 3 hours at room temperature. Acetic acid (21.2 ml.) is added and the reaction is heated for 45 minutes at 100°. The reaction mixture is concentrated to dryness, taken into ethyl acetate, and washed neutral with saturated sodium bicarbonate and dilute hydrochloric acid. The crude product (9.87 g.) is chromatographed twice on silica gel in ethyl acetate:benzene (2:1) to yield 1.9 g. of (±)-1-[[[3-(benzoylamino)-7-[[(phenylmethoxy)carbonyl]amino]-2-oxoheptyl]methylamino]carbonyl]-L-proline, phenylmethyl ester.

(d) (±)-1-[[[3-(Benzoylamino)-7-[[(phenylmethoxy)carbonyl]amino]-2-hydroxyheptyl]methylamino]carbonyl]-L-proline, phenylmethyl ester The ester product from part (c) is treated with sodium borohydride according to the procedure of Example 1(f) to yield (±)-1-[[[3-(benzoylamino)-7-[[(phenylmethoxy)carbonyl]amino]-2-hydroxyheptyl]methylamino]carbonyl]-L-proline, phenylmethyl ester.

(e) (±)-1-[[[7-Amino-3-(benzoylamino)-2-hydroxyheptyl]methylamino]carbonyl]-L-proline The ester product from part (d) is taken into 100 ml. of 95% ethanol with stirring. Ammonium chloride (1.45 ml.) and 180 mg. of 10% palladium on carbon catalyst are added. The mixture is stirred overnight under hydrogen, filtered, and concentrated to dryness. The crude product is lyophilized and purified chromatographically to give (±)-1-[[[7-amino-3-(benzoylamino)-2-hydroxyheptyl]methylamino]carbonyl]-L-proline.

EXAMPLE 68

(±)-1-[[[3-(Benzoylamino)-4-(1H-indol-3-yl)-2-hydroxybutyl]methylamino]carbonyl]-L-proline (a) N-Benzoyl-L-tryptophan L-Tryptophan (61.2 g., 300 mmole) is taken into 600 ml. of 0.5N sodium hydroxide with stirring in an ice bath. Benzoyl chloride (38.3 ml., 330 mmole) and 1N sodium hydroxide (330 ml.) are added over a 25 minute period in 5 equal portions. After 15 minutes the bath is removed and the reaction proceeds for 2 hours at room temperature. The reaction mixture is extracted with ethyl acetate and the aqueous portion is acidified with concentrated hydrochloric acid and extracted into ethyl acetate. The crude product (105 g.) is crystallized from ether to yield 103.3 g. of N-benzoyl-L-tryptophan; m.p. 84°–86° (an ether adduct).

(b) 2-Phenyl-4-[(1H-indol-3-yl)methyl]-5-(4H)-oxazolone

N-Benzoyl-L-tryptophan (50 g., 130.74 mmole) is taken into 200 ml. of tetrahydrofuran with stirring in an ice bath. Dicyclohexylcarbodiimide (27 g., 130.74 mmole) in 60 ml. of tetrahydrofuran is added dropwise. After 15 minutes the ice bath is removed and the reaction proceeds overnight. The dicyclohexylurea is filtered off and the filtrate is concentrated to dryness in vacuo. The crude product is crystallized from methanol to give 30.18 g. of 2-phenyl-4-[(1H-indol-3-yl)methyl]-5(4H)-oxazolone; m.p. 141°–143°.

(c) (±)-1-[[[3-(Benzoylamino)-4-(1H-indol-3-yl)-2-oxobutyl]methylamino]carbonyl]-L-proline, phenylmethyl ester 1-[[[(2-Carboxyethyl)methylamino]carbonyl]-L-proline, phenylmethyl ester (3.2 g., 10 mmole) is taken into 33 ml. of dry tetrahydrofuran with stirring at 5°. Oxalyl chloride (1.05 ml., 12 mmole) is added dropwise followed by 4 drops of dimethylformamide. After 20 minutes the ice bath is removed and after stirring for one hour at room temperature the reaction mixture is concentrated to dryness, taken into 20 ml. of tetrahydrofuran, chilled and added dropwise to 2-phenyl-4-[(1H-indol-3-yl)methyl]-5(4H)-oxazolone (3.0 g., 10.5 mmole) in 16 ml. of dry tetrahydrofuran with stirring in an ice bath. Triethylamine (1.7 ml., 12 mmole) is then added to the reaction mixture. After 15 minutes the ice bath is removed and the reaction is run overnight at room temperature. The triethylamine hydrochloride salt is filtered off and the filtrate is concentrated to dryness, taken into 10.6 ml. of pyridine, 33.3 mg. of 4-dimethylamino pyridine is added, and the mixture is stirred for 3 hours. Acetic acid (10.6 ml.) is added and the reaction is heated for 45 minutes at 100° under an argon atmosphere. The reaction mixture is concentrated to dryness, taken into ethyl acetate, and washed with saturated sodium bicarbonate and dilute hydrochloric acid. The crude product (4.6 g.) is purified on a silica gel column in ethyl acetate:benzene (2:1) to yield 523 mg. of (±)-1-[[[3-(benzoylamino)-4-(1H-indol-3-yl)-2-oxobutyl]methylamino]carbonyl]-L-proline, phenylmethyl ester.

(d) (±)-1-[[[3-(Benzoylamino)-4-(1H-indol-3-yl)-2-oxobutyl]methylamino]carbonyl]-L-proline The ester product from part (c) (520 mg., 1 mmole) is taken into 25 ml. of 95% ethanol containing 100 mg. of palladium on carbon catalyst (10%) and the mixture is stirred under positive hydrogen pressure overnight. The reaction mixture is filtered and concentrated to dryness. The crude product (400 mg.) is purified on a silica gel column with chloroform:methanol:acetic acid (90:5:5) to give 212 mg. of (±)-1-[[[3-(benzoylamino)-4-(1H-indol-3-yl)-2-oxobutyl]methylamino]carbonyl-L-proline; m.p. 102°–128°; $[\alpha]_D^{23}$ −1.3° (c=0.91, methanol). $R_f$ 0.41 (silica gel; chloroform:methanol:acetic acid, 90:5:5)

Anal. calc'd. for $C_{26}H_{28}N_4O_5 \cdot 0.96 H_2O$: C, 63.23; H, 6.11; N, 11.35. Found: C, 63.23; H, 5.92; N, 11.01.

(e)
(±)-1-[[[3-(Benzoylamino)-4-(1H-indol-3-yl)-2-hydroxybutyl]methylamino]carbonyl]-L-proline The product from part (d) is treated with sodium borohydride according to the procedure of Example 1(f) to yield (±)-1-[[[3-(benzoylamino)-4-(1H-indol-3-yl)-2-hydroxybutyl]methylamino]carbonyl]-L-proline.

EXAMPLE 69

(±)-1-[[[3-(Benzoylamino)-4-(4-hydroxyphenyl)-2-hydroxybutyl]methylamino]carbonyl]-L-proline (a)
2-Phenyl-4-[[4-(phenylmethoxy)phenyl]methyl]-5(4H)-oxazolone O-Benzyl-L-tyrosine (11.0 g., 40.5 mmole) is taken into 0.5N sodium hydroxide (81 ml.) and water (81 ml.) with vigorous stirring in an ice-bath. To this in five equal portions is added a total of 52 ml. of benzoyl chloride, 45 ml. of 1N sodium hydroxide and an additional 400 ml. of water over a 25 minute period. The bath is removed and the reaction is run for 2 hours at room temperature. The mixture is extracted twice with ethyl acetate. The aqueous portion is filtered, acidified with 1N hydrochloric acid and the crystals filtered to give 12.9 g. of N-benzoyl-O-benzyl-L-tyrosine; m.p. 166°–168° (162°).

This N-benzoyl-O-benzyl-L-tyrosine (12.76 g., 35 mmole) is taken into dry tetrahydrofuran (50 ml.) with stirring in an ice-bath. To this dicyclohexylcarbodiimide (7.7 g., 37.4 mmole) in tetrahydrofuran (18 ml.) is added dropwise. After 20 minutes, the ice-bath is removed and the reaction proceeds overnight at room temperature. The dicyclohexylurea is filtered off and the filtrate is concentrated to dryness. The crude product is crystallized from ether/hexane to give 10.26 g. of 2-phenyl-4-[[4-(phenylmethoxy)phenyl]methyl]-5(4H)-oxazolone; m.p. 85°–87° (83°).

(b)
(±)-1-[[[3-(Benzoylamino)-2-oxo-4-[4-(phenylmethoxy)phenyl]butyl]methylamino]carbonyl]-L-proline, phenylmethyl ester 1-[[(2-Carboxyethyl)methylamino]carbonyl]-L-proline, phenylmethyl ester (6.4 g., 20 mmole) is taken into 65 ml. of dry tetrahydrofuran with stirring in an ice bath. Oxalyl chloride (2.1 ml., 24 mmole) is added dropwise followed by 15 drops of dimethylformamide. After 20 minutes the ice bath is removed and the reaction proceeds for one hour at room temperature. The reaction mixture is concentrated to dryness, taken into 40 ml. of tetrahydrofuran and added dropwise to a solution of 2-phenyl-4-[[4-(phenylmethoxy)phenyl]methyl]-5(4H)-oxazolone (7.5 g., 21 mmole) in 30 ml. of tetrahydrofuran while stirring in an ice bath. Triethylamine (2.8 ml., 20 mmole) is then added to the reaction mixture. After 30 minutes the ice bath is removed and the reaction is run overnight at room temperature. The triethylamine hydrochloride salt is filtered off and the filtrate is concentrated to dryness in vacuo. The crude residue is taken in 21 ml. of pyridine, 67 mg. of 4-dimethylamino pyridine is added, and the mixture is stirred for 3 hours under an argon blanket. Acetic acid (21 ml.) is added and the reaction mixture is heated for 45 minutes at 100° with stirring under a constant stream of argon. The reaction mixture is concentrated to dryness, taken into ethyl acetate and washed neutral with saturated sodium bicarbonate and dilute hydrochloric acid. The crude product (11.9 g.) is chromatographed over 600 g. of silica gel with ethyl acetate:benzene (2:1) to yield 4.6 g. of (±)-1-[[[3-(benzoylamino)-2-oxo-4-[4-(phenylmethoxy)phenyl]butyl]methylamino]carbonyl]-L-proline, phenylmethyl ester.

(c)
(±)-1-[[[3-(Benzoylamino)-2-hydroxy-4-[4-(phenylmethoxy)phenyl]butyl]methylamino]carbonyl]-L-proline, phenylmethyl ester The ester product from part (b) is treated with sodium borohydride according to the procedure of Example 1(f) to yield (±)-1-[[[3-(benzoylamino)-2-hydroxy-4-[4-(phenylmethoxy)phenyl]butyl]methylamino]carbonyl]-L-proline, phenylmethyl ester.

(d)
(±)-1-[[[3-(Benzoylamino)-4-(4-hydroxyphenyl)-2-hydroxybutyl]methylamino]carbonyl]-L-proline The ester product from part (c) is taken up into 125 ml. of methanol containing 400 mg. of palladium on carbon catalyst (10%) and stirred under positive hydrogen pressure for 20 hours. The reaction mixture is filtered and concentrated to dryness in vacuo. The crude product is purified chromatographically to yield (±)-1-[[[3-(benzoylamino)-4-(4-hydroxyphenyl)-2-hydroxybutyl]methylamino]carbonyl]-L-proline.

EXAMPLE 70

(±)-1-[[[3-(Benzoylamino)-2-hydroxy-4-(3-pyridinyl)butyl]methylamino]carbonyl]-L-proline (a) 2-(Benzoylamino)-3-(3-pyridinyl)-2-propenoic acid 3-Phenyl-4-(3-pyridinylmethylene)-5(4H)-oxazolone (3 g., 12 mmole) [see Griffith et al., J. Org. Chem., Vol. 29, p 2659] is dissolved in acetic acid (24 ml.) and aqueous hydrochloric acid (0.5N, 150 ml.). The reaction mixture is stirred overnight at room temperature. It is evaporated and reevaporated from absolute ethanol. It is triturated with tetrahydrofuran, filtered, and the filtered solid is retriturated with absolute ethanol to yield 2.8 g. of 2-(benzoylamino)-3-(3-pyridinyl)-2-propenoic acid; m.p. 215°–216° (203°).

(b) 2-(Benzoylamino)-3-(3-pyridinyl)propanoic acid 2-(Benzoylamino)-3-(3-pyridinyl)-2-propenoic acid (14 g., 46 mmoles) is dissolved in water (500 ml.) and hydrogenated using palladium on carbon catalyst (10%, 1.8 g.) overnight. The catalyst is filtered off, and the reaction mixture is evaporated to a small volume (100 ml.) and lyophilized to give 13.1 g. of product. The lyophilate is triturated with absolute ethanol-ether mixture and filtered to give 12 g. of 2-(benzoylamino)-3-(3-pyridinyl)propanoic acid; m.p. 99°–115°.

(c)
(±)-1-[[[3-(Benzoylamino)-2-oxo-4-(3-pyridinyl)butyl]methylamino]carbonyl]-L-proline, phenylmethyl ester 2-(Benzoylamino)-3-(3-pyridinyl)propanoic acid (3 g., 9.8 mmole) is suspended in tetrahydrofuran (30 ml.) and while stirring in an ice bath triethylamine (1.4 ml., 10 mmole) and dicyclohexylcarbodiimide (2.1 g., 10.2 mmole) are added. The reaction mixture is stirred at room temperature overnight. It is then filtered and the filtrate is evaporated to dryness. This oxazolone is then dissolved in tetrahydrofuran (15 ml.).

1-[[(2-Carboxyethyl)methylamino]carbonyl]-L-proline, phenylmethyl ester (3 g., 9.4 mmole) is taken into dry tetrahydrofuran and treated with oxalyl chloride and dimethylformamide as set forth in Example 66(g). The resulting acid chloride is taken into tetrahydrofuran (15 ml.), chilled, and added dropwise to the above oxazolone tetrahydrofuran solution while stirring in an ice bath. Triethylamine (1.6 ml., 11.4 mmole) is added and the reaction mixture is stirred at room temperature overnight. Triethylamine hydrochloride salt is filtered off and the filtrate is evaporated in vacuo. The concentrated residue is redissolved in pyridine (10 ml.), 4-dimethylamino pyridine (50 mg.) is added, and the solution is stirred at room temperature for 3 hours. Acetic acid (11 ml.) is then added and the reaction mixture is heated at 100° for 40 minutes. It is then evaporated, redissolved in ethyl acetate and extracted with aqueous saturated sodium bicarbonate solution followed by water. The remaining ethyl acetate extract is concentrated and chromatographed over silica gel using the solvent system ethyl acetate:methanol (95:5) to give 0.8 g. of (±)-1-[[[3-(benzoylamino)-2-oxo-4-(3-pyridinyl)butyl]methylamino]carbonyl]-L-proline, phenylmethyl ester.

(d)
(±)-1-[[[3-(Benzoylamino)-2-oxo-4-(3-pyridinyl)butyl]methylamino]carbonyl]-L-proline The ester product from part (c) (0.7 g., 1.32 mmole) is dissolved in ethanol (50 ml.). Palladium on carbon catalyst (10%, 100 mg.) is added and the solution is stirred under an atmosphere of hydrogen overnight. It is filtered and the filtrate evaporated (0.6 g.). This material is chromatographed over silica gel using the solvent system chloroform:methanol:acetic acid (8:1:1) to yield 0.35 g. of crude product. This is combined with additional material (0.15 g.) of similar purity from another run of the reaction and the combined material (0.5 g.) is applied to a AG-50(H+) column (10 ml. bed volume). The column is washed with water (100 ml.) and then the product is eluted out with 2% aqueous pyridine. The fractions containing the product are pooled, evaporated, redissolved in water and lyophilized to give 0.38 g. of (±)-1-[[[3-(benzoylamino)-2-oxo-4-(3-pyridinyl)butyl]methylamino]carbonyl]-L-proline; m.p. 92°–120°; $[\alpha]_D^{22} = -6.9°$ (c=1.1, methanol). $R_f$ 0.24 (silica gel; chloroform:methanol:acetic acid 8:1:1)

Anal. calc'd. for $C_{23}H_{26}N_4O_5 \cdot 0.9H_2O$: C, 60.75; H, 6.16; N, 12.32. Found: C, 60.74; H, 5.91; N, 12.35.

(e)
(±)-1-[[[3-(Benzoylamino)-2-hydroxy-4-(3-pyridinyl)butyl]methylamino]carbonyl]-L-proline The product from part (d) is treated with sodium borohydride according to the procedure of Example 1(f) to yield (±)-1-[[[3-(benzoylamino)-2-hydroxy-4-(3-pyridinyl)butyl]methylamino]carbonyl]-L-proline.

EXAMPLE 71

1-[[(4-Aminobutyl)[3-(benzoylamino)-2-hydroxy-4-phenylbutyl]amino]carbonyl]-L-proline, monohydrochloride (a)
N-[(Phenylmethoxy)carbonyl]-4-hydroxybutylamine 4-Hydroxybutylamine (10 g., 112.18 mmole) is taken into 200 ml. of dry tetrahydrofuran with stirring in an ice bath. Triethylamine (17.2 ml., 123.4 mmole) is added dropwise followed by phenylmethoxycarbonyl chloride (17.6 ml., 123.4 mmole). After one hour the bath is removed and the reaction proceeds overnight at room temperature. The mixture is concentrated to dryness in vacuo, taken into ethyl acetate and washed with water. The crude product is crystallized from ethyl acetate/hexane to give 16.34 g. of N-[(phenylmethoxy)carbonyl]-4-hydroxybutylamine.

(b) N-[(Phenylmethoxy)carbonyl]-4-bromobutylamine

N-[(Phenylmethoxy)carbonyl]-4-hydroxybutylamine (16.07 g., 72 mmole) and triphenylphosphine (20.75 g., 79 mmole) are taken into 105 ml. of dry tetrahydrofuran into a 3-necked flask stirring and fitted with a condenser. N-Bromosuccinimide (14.1 g., 79 mmole) is added portionwise over a 10 minute period. After 45 minutes the mixture is concentrated to dryness, crystallized from hexane:ethyl acetate (3:1) to remove triphenylphosphine oxide, and the mother liquor is concentrated to dryness to yield 20 g. of crude product. This is purified on 200 g. silica gel in hexane:ethyl acetate (3:1) to yield 14.1 g. of N-[(phenylmethoxy)carbonyl]-4-bromobutylamine.

(c)
N-[[[(Phenylmethoxy)carbonyl]amino]butyl]-glycine, 1,1-dimethylethyl ester

N-[(Phenylmethoxy)carbonyl]-4-bromobutylamine (6.86 g., 24 mmole) and glycine, 1,1-dimethylethyl ester (4.722 g., 36 mmole) are taken into 48 ml. of dimethylformamide. Triethylamine (3.36 ml., 24 mmole) is added to the reaction mixture. After 72 hours at room temperature, sodium bicarbonate (6 g.) is added and after 1.5 hours the mixture is filtered and concentrated to dryness in vacuo. The residue is purified on silica gel in methanol:ethyl acetate (5:95) to give 5.63 g. of N-[[[(phenylmethoxy)carbonyl]amino]butyl]glycine, 1,1-dimethylethyl ester.

(d)
1-[[[[(1,1-Dimethylethoxy)carbonyl]methyl][[[(phenylmethoxy)carbonyl]amino]butyl]amino]carbonyl]-L-proline, phenylmethyl ester L-proline, phenylmethyl ester, hydrochloride (2.364 g., 9.81 mmole) is taken into 39 ml. of methylene chloride with stirring at −20°. N-methylmorpholine (2.76 ml., 24.48 mmole) is added followed by the dropwise addition of phosgene (14.7 mmole, 15.6 ml. of 12.5% solution in benzene). After 30 minutes at −20°, the mixture is concentrated to dryness in vacuo. The residue is taken into 30 ml. of methylene chloride and added dropwise to N-[[[(phenylmethoxy)carbonyl]amino]butyl]glycine,1,1-dimethylethyl ester (3.0 g., 8.916 mmole) in 6 ml. of methylene chloride with stirring in an ice bath. N-methylmorpholine (1.08 ml., 9.8 mmole) is added and after one hour the bath is removed and the reaction proceeds overnight at room temperature. The mixture is concentrated to dryness in vacuo, taken into ethyl acetate and washed neutral with 10% potassium bisulfate and saturated sodium bicarbonate. The crude product is purified on 125 g. of silica gel in ethyl acetate:cyclohexane (2:1) to give 5.7 g. of 1-[[[[(1,1-dimethylethoxy)carbonyl]methyl][[[(phenylmethoxy)carbonyl]amino]butyl]amino]carbonyl]-L-proline, phenylmethyl ester.

(e)
1-[[(Carboxymethyl)[[[(phenylmethoxy)carbonyl]amino]butyl]amino]carbonyl]-L-proline, phenylmethyl ester The ester product from part (d) (5.0 g., 8.8 mmole) is treated for 1.5 hours with 25 ml. of trifluoroacetic acid and 2.1 ml. of anisole, concentrated to dryness and treated twice with cold ether/hexane and decanted. The crude product (4.7 g.) is purified on 250 g. of silica gel in chloroform:methanol:acetic acid (90:5:5) to give 2.77 g. of 1-[[(carboxymethyl)[[[(phenylmethoxy)carbonyl]amino]butyl]amino]carbonyl]-L-proline, phenylmethyl ester.

(f)
1-[[[3-(Benzoylamino)-2-oxo-4-phenylbutyl]][[(phenylmethoxy)carbonyl]amino]butyl]amino]carbonyl]-L-proline, phenylmethyl ester The ester product from part (e) (2.7 g. 5.27 mmole) is taken into 17 ml. of dry tetrahydrofuran with stirring in an ice bath. Oxalyl chloride (0.55 ml., 5.8 mmole) is added dropwise followed by the addition of 4 drops of dimethylformamide. After 20 minutes the bath is removed and after an additional hour the mixture is concentrated to dryness. The residue is taken into 10 ml. of tetrahydrofuran with stirring in an ice bath. 2-Phenyl-4-phenylmethyl-5(4H)-oxazolone (1.33 g., 5.27 mmole) in 8 ml. of tetrahydrofuran is added dropwise followed by triethylamine (0.9 ml., 6.42 ml.). After 30 minutes the bath is removed and the reaction proceeds at room temperature. The triethylamine hydrochloride salt is filtered off and the filtrate is concentrated to dryness in vacuo. The residue is stirred under an argon blanket in 5.6 ml. of pyridine and 25 mg. of 4-dimethylamino pyridine for 3 hours at room temperature. Acetic acid (5.6 ml.) is added and the mixture is heated at 100° for 45 minutes under a gentle argon flow. The mixture is concentrated to dryness, taken into ethyl acetate and washed neutral with saturated sodium bicarbonate and dilute hydrochloric acid. The crude product is purified on a silica gel column in ethyl acetate:benzene (1:1) to give 450 mg. of 1-[[[3-(benzoylamino)-2-oxo-4-phenylbutyl]][[(phenylmethoxy)carbonyl]amino]butyl]amino]carbonyl]-L-proline, phenylmethyl ester.

(g)
1-[[[3-(Benzoylamino)-2-hydroxy-4-phenylbutyl]][[(phenylmethoxy)carbonyl]amino]butyl]amino]carbonyl]-L-proline, phenylmethyl ester The ester product from part (f) is treated with sodium borohydride according to the procedure of Example 1(f) to yield 1-[[[3-(benzoylamino)-2-hydroxy-4-phenylbutyl]][[(phenylmethoxy)carbonyl]amino]butyl]amino]carbonyl]-L-proline, phenylmethyl ester.

(h)
1-[[(4-Aminobutyl)[3-(benzoylamino)-2-hydroxy-4-phenylbutyl]amino]carbonyl]-L-proline, monohydrochloride The ester product from part (g) is taken into 40 ml. of 95% ethanol, 0.584 ml. of 1N hydrochloric acid, and 50 mg. of palladium on carbon catalyst (10%). The mixture is stirred under hydrogen pressure for 24 hours. The reaction mixture is then filtered and concentrated to dryness in vacuo. The crude product is purified on an LH-20 column in water to yield 1-[[(4-aminobutyl)[3-(benzoylamino)-2-hydroxy-4-phenylbutyl]amino]carbonyl]-L-proline, monohydrochloride.

EXAMPLES 72–96

Following the procedure of Examples 65–71 the amino or imino acid ester shown in Col. I is reacted with the oxazolone of Col. II to yield the keto ester product of Col. III. Treatment with a reducing agent such as sodium borohydride yields the hydroxy substituted ureido product shown in Col. IV.

| | Col. I | Col. II | Col. III | Col. IV | | | |
|---|---|---|---|---|---|---|---|
| | HOOC—(CH$_2$)$_n$—N—C—X<br>  　　　　　　　　　|　　\|\|<br>  　　　　　　　　　R$_1$　O | R$_2$—C=N—HC—R$_3$<br>  　　　　\|　　\|<br>  　　　　O—C=O | R$_3$—CH—C—(CH$_2$)$_n$—N—C—X<br>  　\|　　\|\|　　　　　　　\|　\|\|<br>  　NH　O　　　　　　　R$_1$　O<br>  　\|<br>  　C=O<br>  　\|<br>  　R$_2$ | R$_3$—CH—CH—(CH$_2$)$_n$—N—C—X<br>  　\|　　\|　　　　　　　　\|　\|\|<br>  　NH　OH　　　　　　　R$_1$　O<br>  　\|<br>  　C=O<br>  　\|<br>  　R$_2$ | | | |
| Example | R$_3$ | R$_2$ | R$_1$ | X | n |
| 72 | PhCH$_2$— | Ph | H$_3$C— | ![dithiolane-CH$_2$-CH(COOC(CH$_3$)$_3$)-N-]  (L) | 2 |
| 73 | PhCH$_2$— | 4-F-C$_6$H$_4$-CH$_2$ | H$_5$C$_2$— | cyclohexyl-CH(CH$_2$Ph)-CH$_2$-CH(COOCH$_2$Ph)-N- (L) | 2 |
| 74 | —(CH$_2$)$_4$— | 4-H$_3$C-C$_6$H$_4$— | PhCH$_2$— | Ph-CH(CH$_2$Ph)-CH$_2$-CH(COOC(CH$_3$)$_3$)-N- (L) | 1 |

-continued

| | Col. I | Col. II | Col. III | Col. IV | | | |
|---|---|---|---|---|---|---|---|
| | HOOC—(CH$_2$)$_n$—N—C—X with R$_1$ and O | R$_2$—C=N / HC—R$_3$ / O=C—O | R$_3$—CH—(CH$_2$)$_n$—C—N—C—X with NH, C=O, R$_2$, R$_1$, O | R$_3$—CH—CH—(CH$_2$)$_n$—N—C—X with OH, NH, C=O, R$_2$, R$_1$, O | | | |
| Example | R$_3$ | R$_2$ | R$_1$ | X | n | | |
| 75 | thiophen-2-yl-CH$_2$— | —(CH$_2$)$_2$—C$_6$H$_5$ | H$_3$C— | —N(CH$_2$-C$_6$H$_4$)-CH(COOCH(C$_6$H$_5$)$_2$)H (L) | 2 | | |
| 76 | cyclopentyl-CH$_2$— | —C$_6$H$_5$ | F$_3$C— | —N(C$_6$H$_4$)-CH(COOC(CH$_3$)$_3$)H (L) | 1 | | |
| 77 | H— | thiophen-2-yl-CH$_2$— | C$_6$H$_5$-CH$_2$-N=CH-CH$_2$— | —N(CH$_2$-S)-CH(COOC(CH$_3$)$_3$)H (L) | 2 | | |
| 78 | H$_3$C—(H$_2$C)$_3$— | pyridin-2-yl-CH$_2$— | H$_3$C— | —N(-(CH$_2$)$_3$-)-CH(COOCH$_2$C$_6$H$_5$)H (L) | 1 | | |

-continued

| | Col. I | Col. II | Col. III | Col. IV | |
|---|---|---|---|---|---|
| | HOOC—(CH$_2$)$_n$—N(R$_1$)—C(O)—X | R$_2$—C(=N—HC—R$_3$)(—O—C(=O)—) | R$_3$—CH(—NH—C(=O)—R$_2$)—C(=O)—(CH$_2$)$_n$—N(R$_1$)—C(O)—X | R$_3$—CH(OH)—CH(—NH—C(=O)—R$_2$)—(CH$_2$)$_n$—N(R$_1$)—C(O)—X | |
| Example | R$_3$ | R$_2$ | R$_1$ | X | n |
| 79 | 2-pyridyl—(CH$_2$)$_2$— | phenyl | phenyl-C(=O)-CH$_2$-CH(NH—)(H$_2$C)$_4$— | piperidine-2-COOC(CH$_3$)$_3$ (L) | 2 |
| 80 | phenyl | benzyl (—CH$_2$-C$_6$H$_5$) | O$_2$N—HN—C(=NH)—HN—(H$_2$C)$_3$— | 1,3-dithiolane-2-COOC(CH$_3$)$_3$ (L) | 2 |
| 81 | O$_2$N—HN—C(=NH)—HN—(H$_2$C)$_3$— | benzyl | H$_3$C— | 2-benzyl(thio)-pyrrolidine-COOC(CH$_3$)$_3$ (L) | 1 |
| 82 | indol-3-yl-CH$_2$— | 4-pyridyl-CH$_2$— | H$_3$C— | 2-(2-phenoxyethyl)-pyrrolidine-COOC(CH$_3$)$_3$ (L) | 2 |

-continued

| | Col. I | Col. II | Col. III | Col. IV | |
|---|---|---|---|---|---|
| | HOOC—(CH$_2$)$_n$—N(R$_1$)—C(=O)—X | R$_2$—C(=N—HC—R$_3$)—O—C(=O) | R$_3$—CH(NH—C(=O)—R$_2$)—C(=O)—(CH$_2$)$_n$—N(R$_1$)—C(=O)—X | R$_3$—CH(OH)—CH(NH—C(=O)—R$_2$)—(CH$_2$)$_n$—N(R$_1$)—C(=O)—X | |
| Example | R$_3$ | R$_2$ | R$_1$ | X | n |
| 83 | 3,5-bis(benzyloxy)phenyl (H$_2$CO—C$_6$H$_3$(—CH$_2$—)—OCH$_2$—C$_6$H$_5$) | —CH$_2$—C$_6$H$_5$ | H$_3$C—(CH$_2$)$_2$— | piperidinyl-CH(COOC(CH$_3$)$_3$)—H (L) | 1 |
| 84 | —C$_6$H$_5$ | —CH$_2$—C$_6$H$_5$ | cyclohexyl | —NH—CH(CH$_2$OCH$_2$—C$_6$H$_5$)—COOC(CH$_3$)$_3$ (L) | 1 |
| 85 | —C$_6$H$_5$ | —CH$_2$—(2-pyridyl) | —CH$_2$—C$_6$H$_5$ | —NH—CH(CH$_2$—C$_6$H$_5$)—COOC(CH$_3$)$_3$ (L) | 2 |
| 86 | 2-thienyl-CH$_2$— | —CH$_2$—C$_6$H$_5$ | H$_3$C— | —NH—CH(CH$_2$—C$_6$H$_4$—OCH$_2$—C$_6$H$_5$)—COOC(CH$_3$)$_3$ (L) | 2 |

-continued

| Example | Col. I<br>R₃—CH—C—(CH₂)ₙ—N—C—X<br>　　　　NH　　R₁　O<br>　　　　C=O<br>　　　　R₂<br>HOOC—(CH₂)ₙ—N—C—X<br>　　　　　　　R₁　O | Col. II<br>R₂—C—N<br>　　　O—C=O<br>　　　　HC—R₃ | Col. III<br>R₃—CH—C—(CH₂)ₙ—N—C—X<br>　　　NH　　R₁　O<br>　　　C=O<br>　　　R₂<br>R₁ | Col. IV<br>OH R₁ O<br>R₃—CH—CH—(CH₂)ₙ—N—C—X<br>　　NH<br>　　C=O<br>　　R₂ | | |
|---|---|---|---|---|---|---|
| | | R₃ | R₂ | R₁ | X | n |
| 87 | | —CH₂—⟨furan⟩ | —⟨phenyl⟩ | H₃C— | —NH—CH—COOC(CH₃)₃ (L)<br>　　　CH₂<br>　　　—N=CH—N—CH₂—⟨phenyl⟩ | 2 |
| 88 | | —CH₂—⟨cyclohexyl⟩ | —⟨phenyl⟩ | H₃C— | —NH—CH—COOC(CH₃)₃ (L)<br>　　　(CH₂)₄—NHCOCH₂—⟨phenyl⟩ | 1 |
| 89 | | —CH₂—⟨phenyl⟩ | —⟨phenyl⟩ | H₃C— | —N—CH₂—COOCH₂—⟨phenyl⟩<br>　⟨phenyl⟩ | 2 |
| 90 | | —CH₂—⟨phenyl⟩ | —⟨phenyl⟩ | H₃C— | ⟨phenyl⟩—CH₂—C(COOCH₂⟨phenyl⟩)(H)—N=N (L) | 2 |

-continued

| | Col. I | Col. II | Col. III | Col. IV | | |
|---|---|---|---|---|---|---|
| | HOOC—(CH₂)ₙ—N(R₁)—C(=O)—X | R₂—C(=N—CH(R₃)—C(=O)—O) (oxazolinone) | R₃—CH(NH—C(=O)—R₂)—C(=O)—N(R₁)—(CH₂)ₙ—N(R₁)—C(=O)—X | R₃—CH(NH—C(=O)—R₂)—CH(OH)—(CH₂)ₙ—N(R₁)—C(=O)—X | | |
| Example | R₃ | R₂ | R₁ | X | n |
| 91 | H₃C— | phenyl | H₃C— | —NH—CH(CH₂CH(CH₃)₂)—COOCH₂-phenyl (L) | 1 |
| 92 | phenyl-(CH₂)₄— | phenyl | F₃C— | —NH—CH((CH₂)₂C(=O)NH₂)—COOC(CH₃)₃ (L) | 2 |
| 93 | phenyl-CH₂— | phenyl | H₃C— | cyclohexyl-CH(O-C(=O)-C₂H₅)-C(=O)-N-CH(CH₂-S-S)-H (L) | 1 |
| 94 | phenyl-CH₂— | phenyl | H₃C— | CH(CH₃)₂-CH(O-C(=O)-C₂H₅)-C(=O)-N-CH((CH₂)ₓ)-H (L) | 1 |

-continued

| Example | Col. I<br>$R_1$ $O$<br>\| \|\|<br>HOOC—$(CH_2)_n$—N——C—X | Col. II<br>$R_2$—C$\overset{N}{\underset{O}{\diagdown}}$$\overset{HC—R_3}{\underset{C=O}{\diagup}}$ | Col. III<br>$R_3$—CH—$\overset{O}{\overset{\|}{C}}$—$(CH_2)_n$—$\overset{R_1}{\underset{\|}{N}}$—$\overset{O}{\overset{\|}{C}}$—X<br>\|<br>NH<br>\|<br>C=O<br>\|<br>$R_2$ | Col. IV<br>$R_3$—CH—CH—$(CH_2)_n$—$\overset{R_1}{\underset{\|}{N}}$—$\overset{O}{\overset{\|}{C}}$—X<br>\|<br>OH NH<br>\|<br>C=O<br>\|<br>$R_2$ | |
|---|---|---|---|---|---|
| | $R_3$ | $R_2$ | $R_1$ | X | n |
| 95 |  pyridyl-$(CH_2)_4$— |  phenyl | $H_3C$— |  —N—CH—C(=O)—O—CH_2—O—C(=O)—C(CH_3)_3 (L) | 2 |
| 96 |  thienyl-$H_2C$— | 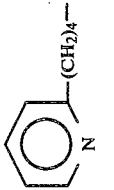 phenyl | $H_3C$— |  —N—CH—C(=O)—O—CH(CH_3)—O—C(=O)—C_2H_5 | 2 |

The R1 protecting groups in Examples 77, 79 and 80, the R3 protecting groups in Examples 81 and 83, and the R5 protecting groups in Examples 84 and 86 to 88 are removed as the last step in the synthesis. The R6 ester groups shown in Examples 93 to 96 are not removed.

EXAMPLE 97

1-[[[(3S)-3-(Benzoylamino)-2-hydroxy-4-phenylbutyl]-methylamino]carbonyl]-L-proline, ethyl ester (isomer A)

1-[[[(3S)-3-(Benzoylamino)-2-hydroxy-4-phenylbutyl]methylamino]carbonyl]-L-proline (isomer A) is treated for several hours at room temperature with 10 ml. of 2N ethanolic hydrochloric acid, concentrated in vacuo, taken up into ethyl acetate and washed neutral with 10% potassium bisulfate and saturated sodium bicarbonate to yield the crude product. This material is purified on silica gel column to give 1-[[[(3S)-3-(benzoylamino)-2-hydroxy-4-phenylbutyl]methylamino]-carbonyl]-L-proline, ethyl ester (isomer A).

In a similar manner, ethyl or other alkyl esters of the compounds of Examples 2 to 58 and 65 to 92 can be prepared.

EXAMPLE 98

1-[[[(3S)-3-(Benzoylamino)-2-hydroxy-4-phenylbutyl]-methylamino]carbonyl]-L-proline, 3-pyridinylmethyl ester (isomer A)

1-[[[(3S)-3-(Benzoylamino)-2-hydroxy-4-phenylbutyl]methylamino]carbonyl]-L-proline (isomer A), 4-dimethylamino pyridine, 3-pyridinylcarbinol and dicyclohexylcarbodiimide are taken up into tetrahydrofuran with stirring in an ice bath. The reaction proceeds overnight at room temperature. The dicyclohexylurea is filtered off and the filtrate is concentrated to dryness. The crude product is chromatographed on silica gel to give 1-[[[(3S)-3-(benzoylamino)-2-hydroxy-4-phenylbutyl]methylamino]carbonyl]-L-proline, 3-pyridinylmethyl ester (isomer A).

EXAMPLES 99–110

Following the procedure of Example 98, 1-[[[(3S)-3-(benzoylamino)-2-hydroxy-4-phenylbutyl]methylamino]carbonyl]-L-proline (isomer A) is treated with the reagent shown below in Col. I to yield the ester product shown in Col. II.

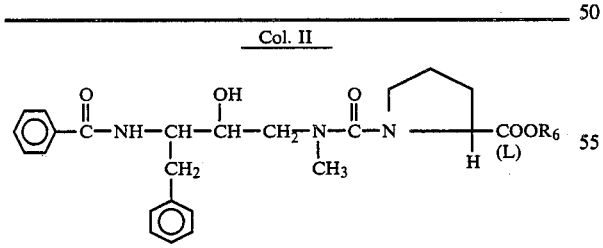
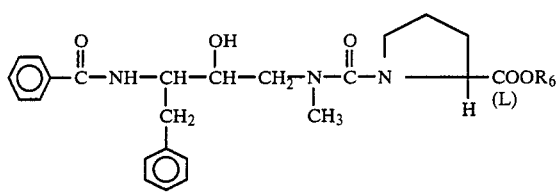

In a similar manner, esters can be prepared of the products of Examples 2 to 58 and 65 to 92.

EXAMPLE 111

1-[[[(3S)-3-(Benzoylamino)-2-hydroxy-4-phenylbutyl]-methylamino]carbonyl]-L-proline, sodium salt (isomer A)

1-[[[(3S)-3-(Benzoylamino)-2-hydroxy-4-phenylbutyl]methylamino]carbonyl]-L-proline (isomer A) (1 mole) is dissolved in water (50 ml.). Aqueous sodium bicarbonate (0.1N, 20 ml.) is added and the aqueous solution is lyophilized. It is then dissolved in water (10 ml.) and applied on a column (5 cm. × 60 cm.) of Sephadex chromatography gel G-10 and eluted with water. Fractions containing the desired product are pooled and lyophilized to obtain 1-[[[(3S)-3-(benzoylamino)-2-hydroxy-4-phenylbutyl]methylamino]carbonyl]-L-proline, sodium salt (isomer A).

EXAMPLE 112

1000 tablets each containing the following ingredients:

| | |
|---|---|
| 1-[[[(3S)—3-(Benzoylamino)-2-hydroxy-4-phenylbutyl]methylamino]carbonyl]-L—proline, sodium salt (isomer A) | 100 mg. |
| Corn starch | 50 mg. |
| Gelatin | 7.5 mg. |
| Avicel(microcrystalline cellulose) | 25 mg. |
| Magnesium stearate | 2.5 mg. |
| | 185 mg. | are prepared from sufficient bulk quantities by mixing the 1-[[[(3S)-3-(benzoylamino)-2-hydroxy-4-phenylbutyl]methylamino]carbonyl]-L-proline, sodium salt (isomer A) and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 110 can be prepared.

A similar procedure can be employed to form tablets containing 50 mg. of active ingredient.

EXAMPLE 113

Two piece #1 gelatin capsules each containing 50 mg. of (trans)-1-[[[(3S)-3-(benzoylamino)-2-hydroxy-4-phenylbutyl]methylamino]carbonyl]-4-cyclohexyl-L-proline, sodium salt are filled with a mixture of the following ingredients:

| | |
|---|---|
| (trans)-1-[[[(3S)—3-(Benzoylamino)-2-hydroxy-4-phenylbutyl]methylamino]carbonyl]-4-cyclohexyl-L—proline, sodium salt | 50 mg. |
| Magnesium stearate | 7 mg. |
| Lactose | 193 mg. |
| | 250 mg. |

In a similar manner capsules containing 50 mg. of the product of any of Examples 1, 2, and 4 to 110 can be prepared.

EXAMPLE 114

An injectable solution is prepared as follows:

| | |
|---|---|
| 1-[[[(3S)—3-(Benzoylamino)-2-hydroxy-4-phenylbutyl]methylamino]carbonyl]-L—proline, sodium salt (isomer A) | 500 g. |
| Methyl paraben | 5 g. |
| Propyl paraben | 1 g. |
| Sodium chloride | 25 g. |
| Water for injection | 5 l |

The active substance, preservatives, and sodium chloride are dissolved in 3 liters of water for injection and then the volume is brought up to 5 liters. The solution is filtered through a sterile filter and aseptically filled into presterilized vials which are closed with pre-sterilized rubber closures. Each vial contains 5 ml. of solution in a concentration of 100 mg. of active ingredient per ml. of soliution for injection.

In a similar manner, an injectable solution containing 100 mg. of active ingredient per ml. of solution can be prepared for the product of any of Examples 2 to 110.

EXAMPLE 115

1000 tablets each containing the following ingredients:

| | |
|---|---|
| 1-[[[(3S)—3-(Benzoylamino)-2-hydroxy-4-phenylbutyl]methylamino]carbonyl]-L—proline, sodium salt (isomer A) | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the 1-[[[(3S)-3-(benzoylamino)-2-hydroxy-4-phenylbutyl]methylamino]carbonyl]-L-proline, sodium salt (isomer A), Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 2 to 110.

What is claimed is:

1. A compound of the formula

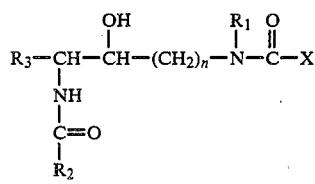

or a pharmaceutically acceptable salt thereof wherein X is

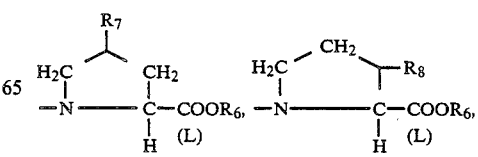

-continued

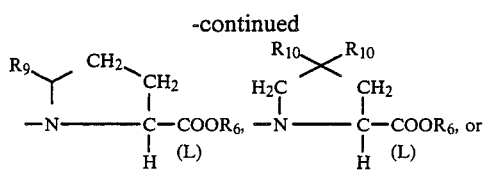

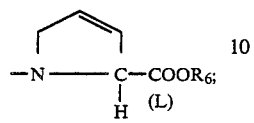

n is one or two;
R₁ is hydrogen, lower alkyl, halo substituted lower alkyl,

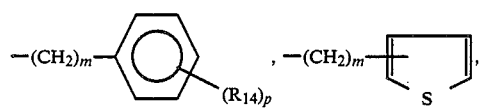

$-(CH_2)_m$—cycloalkyl, $-(CH_2)_2-NH_2$, $-(CH_2)_3-NH_2$,

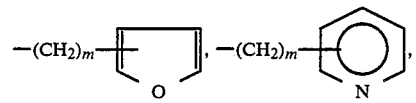

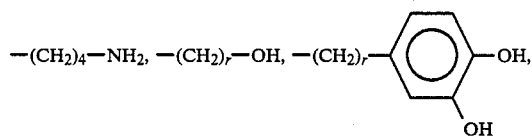

$-(CH_2)_r-SH$, $-(CH_2)_r-S$—lower alkyl,

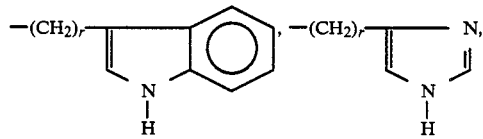

R₂ is 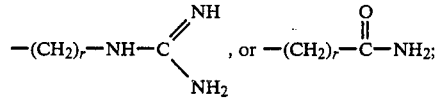

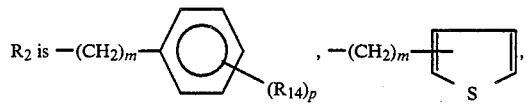

R₃ is hydrogen, lower alkyl,

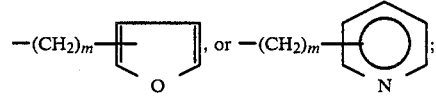

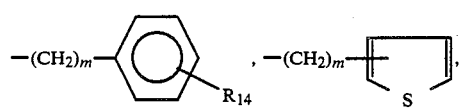

-continued

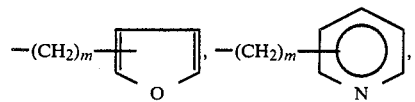

halo substituted lower alkyl, $-(CH_2)_m$-cycloalkyl,

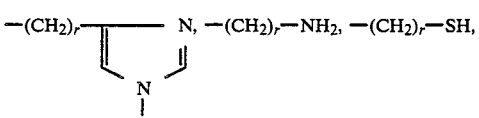

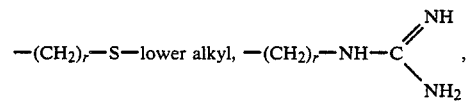

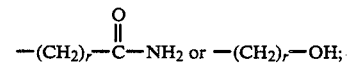

$-(CH_2)_r-S$—lower alkyl, $-(CH_2)_r-NH-C\underset{NH_2}{\overset{NH}{\diagup}}$,

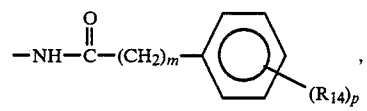

r is an integer from 1 to 4;
R₇ is hydrogen, lower alkyl, halogen, keto, hydroxy,

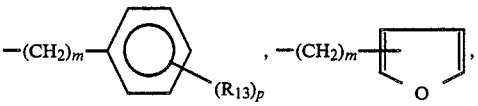

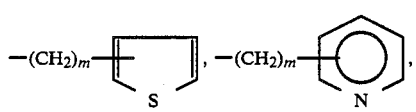

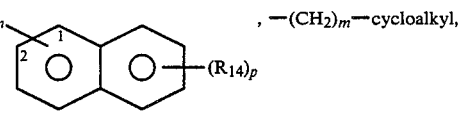

a 1- or 2-naphthyl of the formula

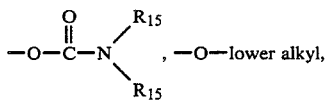

-continued

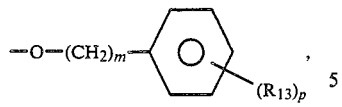

a 1- 2-naphthyloxy of the formula

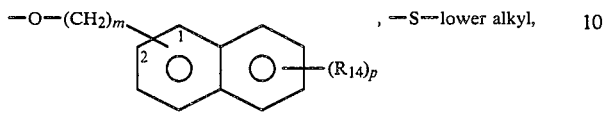

or a 1- 2-naphthylthio of the formula

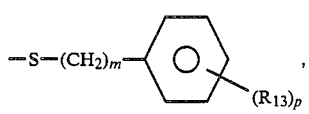

; $R_8$ is keto, halogen,

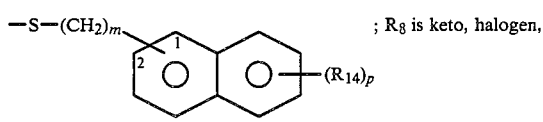

-O-lower alkyl, a 1- or 2-naphthyloxy of the formula

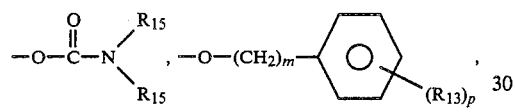

or a 1- or 2-naphthylthio of the formula

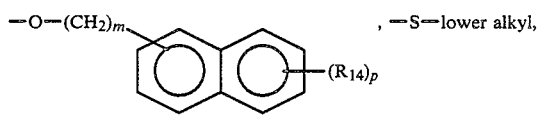

$R_9$ is keto or

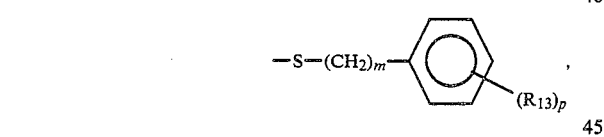

$R_{10}$ is halogen or —Y—$R_{16}$;

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

m is zero, one, two, three, or four;

p is one, two or three provided that p is more than one only if $R_{13}$ or $R_{14}$ is hydrogen, methyl, methoxy, chloro, or fluoro;

$R_{15}$ is hydrogen or lower alkyl of 1 to 4 carbons;

Y ix oxygen or sulfur;

$R_{16}$ is lower alkyl of 1 to 4 carbons, or

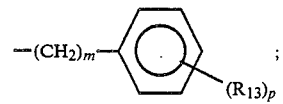

$R_{19}$ is lower alkyl, benzyl, or phenethyl;

$R_{20}$ is hydrogen, lower alkyl, benzyl or phenethyl;

$R_6$ is hydrogen, lower alkyl, benzyl, benzhydryl,

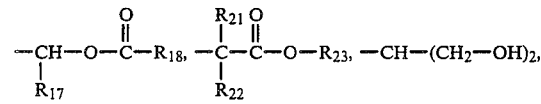

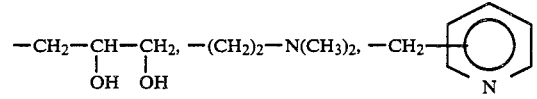

or a pharmaceutically acceptable salt forming ion;

$R_{17}$ is hydrogen, lower alkyl, cycloalkyl, or phenyl;

$R_{18}$ is hydrogen, lower alkyl, lower alkoxy, or phenyl or $R_{17}$ and $R_{18}$ taken together are —(CH$_2$)$_2$—, —(CH$_2$)$_3$—, —CH=CH—, or

$R_{21}$ and $R_{22}$ are independently selected from hydrogen and lower alkyl; and $R_{23}$ is lower alkyl.

2. A compound of claim 1 wherein:

$R_6$ is hydrogen, straight or bramched chain lower alkyl of 1 to 4 carbons, alkali metal salt ion,

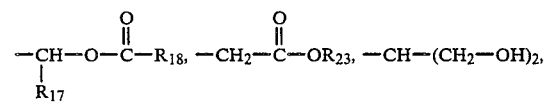

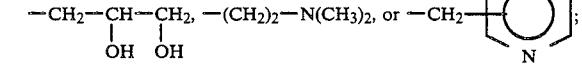

$R_{23}$ is straight or branched chain lower alkyl of 1 to 4 carbons;

$R_7$ is hydrogen, hydroxy, straight or branched chain lower alkyl of 1 to 4 carbons, cyclohexyl, amino, -O-lower alkyl wherein lower alkyl is straight or branched chain of 1 to 4 carbons,

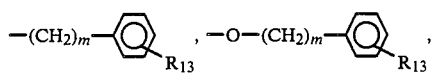

1-naphthyloxy, 2-naphthyloxy, -S-lower alkyl wherein lower alkyl is straight or branched chain of 1 to 4 carbons,

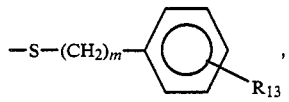

1-naphthylthio, or 2-naphthylthio;
R$_8$ is -O-lower alkyl, -S-lower alkyl,

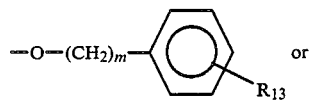 or

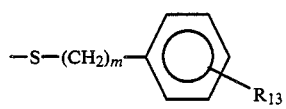

wherein lower alkyl is straight or branched chain of 1 to 4 carbons,
R$_9$ is phenyl, 2-hydroxyphenyl or 4-hydroxyphenyl;
R$_{10}$ are both fluoro, both chloro, or both —Y—R$_{16}$;
Y is O or S;
R$_{16}$ is straight or branched chain lower alkyl of 1 to 4 carbons;
m is zero, one, or two;
R$_{13}$ is hydrogen, methyl, methoxy, methylthio, chloro, bromo, fluoro, or hydroxy;
R$_{17}$ is hydrogen, straight or branched chain lower alkyl of 1 to 4 carbons, or cyclohexyl;
R$_{18}$ is straight or branched chain lower alkyl of 1 to 4 carbons or phenyl.

3. A compound of claim 2 wherein:
R$_2$ is

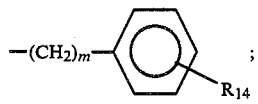

R$_3$ is straight or branched chain lower alkyl of 1 to 4 carbons, —(CH$_2$)$_r$—NH$_2$,

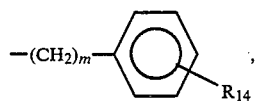

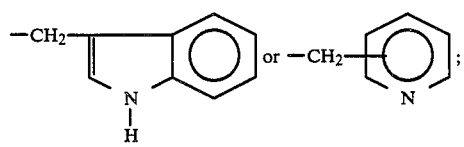

n is one;

R$_1$ is straight or branched chain lower alkyl of 1 to 4 carbons, —CF$_3$, —(CH$_2$)$_2$—NH$_2$, —(CH$_2$)$_3$—NH$_2$, —(CH$_2$)$_4$—NH$_2$,

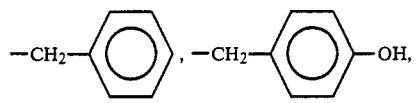

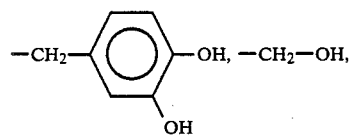

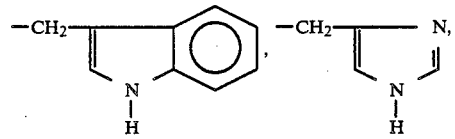

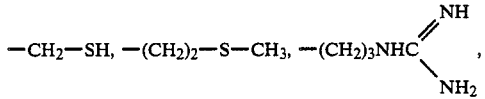

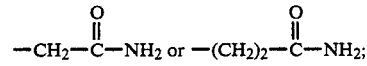

r is an integer from one to four;
m is zero, one, or two; and
R$_{14}$ is hydrogen, methyl, methoxy, methylthio, chloro, bromo, fluoro, or hydroxy.

4. A compound of claim 3 wherein:
X is

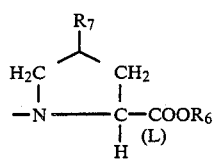

R$_7$ is hydrogen, cyclohexyl, lower alkoxy of 1 to 4 carbons,

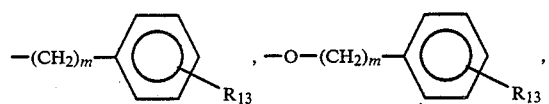

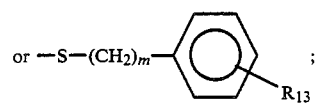

m is zero, one or two;
R$_{13}$ is hydrogen, methyl, methoxy, methylthio, chloro, bromo, fluoro, or hydroxy;
R$_1$ is straight or branched chain lower alkyl of 1 to 4 carbons;
R$_6$ is hydrogen, an alkali metal salt ion,

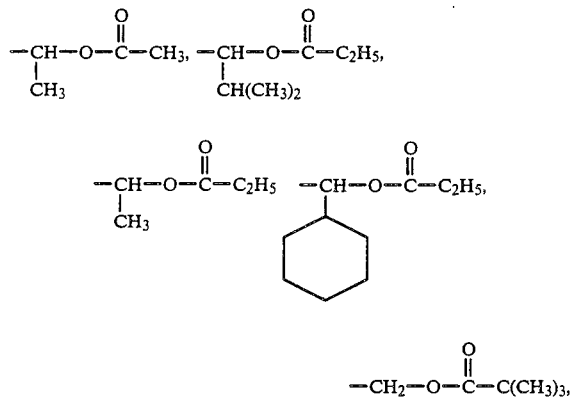

straight or branched chain lower alkyl of 1 to 4 carbons, —(CH$_2$)$_2$N(CH$_3$)$_2$, or

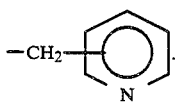

5. A compound of claim 4 wherein:
X is

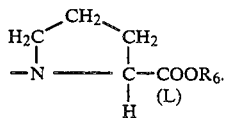

6. A compound of claim 5 wherein:
R$_2$ is phenyl;
R$_3$ is benzyl;
R$_1$ is methyl; and
R$_6$ is hydrogen.

7. The compound of claim 6, 1-[[[(3S)-3-(benzoylamino)-2-hydroxy-4-phenylbutyl]methylamino]-carbonyl]-L-proline (isomer A).

8. The compound of claim 6, 1-[[[(3S)-3-(benzoylamino)-2-hydroxy-4-phenylbutyl]methylamino]-carbonyl]-L-proline (isomer B).

9. A compound of claim 4 wherein
X is

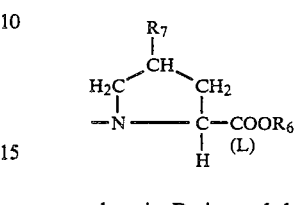

wherein R$_7$ is cyclohexyl.

10. A compound of claim 9 wherein
R$_2$ is phenyl;
R$_3$ is benzyl;
R$_1$ is methyl; and
R$_6$ is hydrogen.

11. The compound of claim 10, (trans)-1-[[[(3S)-3-(benzoylamino)-2-hydroxy-4-phenylbutyl]methylamino]carbonyl]-4-cyclohexyl-L-proline.

12. A pharmaceutical composition useful for treating hypertension comprising a pharmaceutically acceptable carrier and a hypotensively effective amount of a compound of the formula

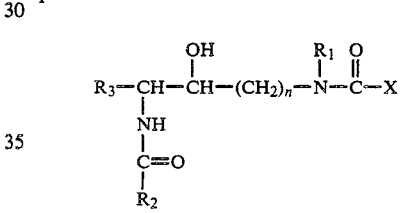

wherein n, R$_1$, R$_2$, R$_3$ and X are as defined in claim 1.

13. The method of treating hypertension in a mammalian host which comprises administering a hypotensively effective amount of the composition of claim 12.

* * * * *